United States Patent [19]

Tsai et al.

[11] Patent Number: 5,837,257
[45] Date of Patent: Nov. 17, 1998

[54] USE OF PLANT EXTRACTS FOR TREATMENT OF HIV, HCV AND HBV INFECTIONS

[75] Inventors: Hsiu-Hsien Tsai, Chang-Huah, Taiwan; Shie-Ming Hwang, Columbus, Ohio; Pai-Chu Kung, Chaug-Huah, Taiwan

[73] Assignee: Sage R&D, Columbus, Ohio

[21] Appl. No.: 863,803

[22] Filed: May 27, 1997

[51] Int. Cl.$^6$ .............................. A61K 35/78; A61K 9/20; A61K 9/48

[52] U.S. Cl. ....................... 424/195.1; 424/451; 424/464; 424/489; 424/456

[58] Field of Search ................................ 424/195.1, 451, 424/464, 456, 489

[56] References Cited

U.S. PATENT DOCUMENTS

| | | | |
|---|---|---|---|
| 4,886,666 | 12/1989 | Liu ........................................ | 424/195.1 |
| 5,178,865 | 1/1993 | Ho et al. ................................ | 424/195.1 |
| 5,366,725 | 11/1994 | Okubo et al. ........................... | 424/85.4 |
| 5,411,733 | 5/1995 | Hozumi et al. ........................ | 424/195.1 |

FOREIGN PATENT DOCUMENTS

| | | |
|---|---|---|
| 1077379A | of 1992 | China . |
| 1079157 | of 1993 | China . |
| 04018019 | of 1992 | Japan . |

OTHER PUBLICATIONS

Nakanishi et al., Shoyakugaku Zasshi, 47:295–300, 1993.
Lin et al., Amer. J. Chin. Med., 18:35–43, 1990.
Tan et al., J. Nat. Prod., 54:143–154, 1991.
Thorne et al., Antiviral Res., 5:335–343, 1985.
Ghazanfar, Handbook of Arabian Medicinal Plants, CRC Press, Inc., Boca Raton, FLA, pp. 200–202, 1994.
Kugach et al., Khim–Farm ZH, 22:471–475, English translation of abstract only, 1988.
Kikuchi et al, Yakugaku Zasshi, 101:575–578, 1981, English translation of abstract only.
Junxian et al., Zhongguo Zhongyao Zazhi, 3:168–170, English translation of abstract only, 1990.
H. Y. Hsu, Y. P. Chen, & M. Hong, *The Chemical Constituents of Oriental Herbs*, vol. 2, Oriental Healing Arts Institute, Los Angeles, California, U.S.A.,51, 53–55, 142–143, 742, 758–759 (1985).
H. Y. Hsu, Y. P. Chen, S. G. Hsu, J. S. Hsu, C. J. Chen, & H. C. Chang, *Concise Pharmacognosy*, New Medicine Publishing Co., Taipei, Taiwan, R.O.C., 90, 97, 105–106, 117–118, 126–127, 130–131, 133, 144–145, 152–153, 156–157, 161–162, 174, 176–177, 357–358, 381–382, 384–385, 456–457, 577–578 (1985).
H. y. Hsu, Y. P. Chen, & M. Hong, *The Chemical Constituents of Oriental Herbs*, Oriental Healing Arts Institute, Los Angeles, California, U.S.A., 114–115, 249–250, 1400–1401, 1406 (1982).
C.–W. Chang, M.–T. Lin, S.–S. Lee, K.C.S.C. Liu, F.–L. Hsu, & J.–Y. Lin, *Antiviral Research*, 27, 367–374 (1995).
P. J. Houghton, Z. Boxu, & Z. Xisheng, *Phytother. Res.*, 7, 384–386 (1993).

Y. Q. Li, W. Yuan & S. L. Zhang, *Chung Kuo Chung Hsi chieh Ho Tsa Chih*, 12(12), 708, 719–721, 737 (1992).
H. J. Yan, *Chung Hsi I Chieh Ho Tsa Chih*, 11(8), 452, 468–470 (1991).
J. F. John, R. Kuk & A. Rosenthal, *Abstr. Gen. Meet. Am. Soc. Microbiol*, 94, 481 (1994).
K. Yamasaki, T. Otake, H. Mori, M. morimoto, N. Ueba, Y. Kurokawa, K. Shiota, & T. Yuge, *Yakugaku Zasshi*, 113(11), 818–824 (1993).
X. J. Yao, M. A. Wainberg, & M. A. Parniak, *Virology*, 187(1), 56–62 (1992).
H. D. Tabba, R. S. Chang, & K. M. Smith, *Antiviral Research*, 11, 263–273 (1989).
M. Zheng, *J. Tradit. Chin. Med.*, 8(3), 203–206 (1988).
S. Y. Ryu, C–K. Lee, C. O. Lee, H. S. Kim, & O. P. Zee, *Arch. Pharmacal Res. (Seoul)*, 15(3), 242–245 (1992).
Y. L. Lin, Y. H. Kuo, G. H. Lee, and S. M. Peng, *J. Chem. Research (S)*, 320–321 (1987).
T. Nagai et al., *Chem Pharm. Bull.*, 38(5), 1329–1332 (1990).
P. Pushpangadan and C. K. Atal, *J. Ethnopharmacol*, 11(1), 59–77 (1984).
M. Takechi & Y. Tanaka, *Planta Medica*, 42, 69–74 (1981).
C. J. M. Kane, et al., *Bioscience Reports*, 8, 85–94 (1988).
H. C. Chang, *Medicinal Herbs I*, Holiday Publishing Co., Taipei, Taiwan, R.O.C., 15, 36, 100, 113, 127, 147 (1990), (No translation).
H. C. Chang, *Medicinal Herbs II*, Holiday Publishing Co., Taipei, Taiwan, R.O.C., 15, 131 135 155 (1991), (No translation).
W. S. Kan, *Pharmaceutical Botany*, National Research Institute of Chinese Medicine, Taipei, Taiwan, R.O.C., 113, 124–130, 200–201, 206–207, 289–290, 353–354, 442–444, 485, 487–488, 497, 505, 513–514, 522, 527–529, 558, 562–563, 648–649 (1971), (No translation).

(List continued on next page.)

*Primary Examiner*—David M. Naff
*Assistant Examiner*—Janet M. Kerr
*Attorney, Agent, or Firm*—Donald O. Nickey; Standley & Gilcrest

[57] ABSTRACT

This invention relates to compositions derived from Chinese herbal medicines, medicinal plants and extracts thereof, and to their use for the treatment of animals infected with viruses, especially with hepatitis B virus (HBV), hepatitis C virus (HCV), and human immunodeficiency virus (HIV). More specifically, the compositions of the present invention are derived from various Chinese herbal medicines or medicinal plants which have a long history of human consumption. The compositions of the invention are obtained through specific techniques and have demonstrated outstanding efficacy for treating human HBV carriers and hepatitic C patients. Compositions according to the invention have also exhibited in vitro antiviral activities against murine leukemia virus (MuLV) and HIV. HIV is the virus known to cause acquired immunodeficiency syndrome (AIDS) in humans and AIDS presents special problems to the medical community which the present invention addresses.

13 Claims, No Drawings

OTHER PUBLICATIONS

M. S. Lee, *Frequently Used Chinese Crude Ddrugs and Folk Medicines Handbook*, 12th Ed., Sheng–Chang Medicinal Record Magazine Publishing Co., Taipei, Taiwan, R.O.C., 4–6, 17, 21, 19, 36, 38, 40, 48, 64, 71, 79, 85 (1992), (No translation).

*Instruction of "Taifu" Serodia–HbsAg Detection*, Taifu Pharmaceutical Co., Ltd., Taoyuan, Taiwan, R.O.C.

D. S. Chen & J. L. Sung, *J. Formosan Med. Assoc.*, 77, 263–270 (1978).

T. Juji & T. Yokochi, Japan. *J. Exp. Med.*, 39, 615–620 (1969).

T. Mosmann, *J. Immunological Methods*, 65, 55–63 (1983).

H. Ruebsamen–Waigmann, et al., *J. Med. Virology*, 19, 335–344 (1986).

Ch. Mueller, et al., *Fresenius Z. Anal. Chem.*, 330, 352–353 (1988).

H. V. Briesen et al., *J. Med. Virology*, 23, 51–66 (1987).

*Instruction of Kyokuto TA–E Transaminade Assay Reagents*, Permit No. (62 AM)0885, Kyokkkuto Pharmaceutical Industry Co., Ltd., Tokyo, Japan, 1994.

*Instruction of Yatrozyme TA–Lq Transaminase–assay Reagent Solution (Enzyme Assay)*, Commodity No. 817245 (RM 163–K), Yatron Co., Ltd., Diayatron Co., Ltd., Tokyo, Japan.

U. Lippi & G Guidi, *Clin. Chim. Acta.*, 28, 431–437 (1970).

Kuo, et al., Scutellaric Acid, a New Triterpene from *Scutellaria rivularis*, *Chem. Pharm. Bull.* 36 (9), 3619–3622 (1988).

USE OF PLANT EXTRACTS FOR TREATMENT OF HIV, HCV AND HBV INFECTIONS

RELATED APPLICATIONS

This application claims priority to a provisional application filed Jul 9, 1996, Ser. No. 60/016,100 entitled: ANTI-VIRAL AGENTS; and to a provisional application filed Jul. 10, 1996, Ser. No. 60/021,467 entitled: ANTI-VIRAL AGENTS FROM CHINESE MEDICINAL HERBS.

ADVANCEMENT OF EXAMINATION

This application is being filed with a Petition to Make the Application Special under 37 C.F.R. §1.102(d) accompanied by the fee set forth in 37 C.F.R. §1.17(i).

TECHNICAL FIELD

This invention relates to compositions derived from Chinese herbal medicines, medicinal plants and extracts thereof, and to their use for the treatment of animals infected with viruses, especially with hepatitis B virus (HBV), hepatitis C virus (HCV), and human immunodeficiency virus (HIV). More specifically, the compositions of the present invention are derived from various Chinese herbal medicines or medicinal plants which have a long history of human consumption. The compositions of the invention are obtained through specific techniques and have demonstrated outstanding efficacy for treating human HBV carriers and hepatitic C patients. Compositions according to the invention have also exhibited in vitro antiviral activities against murine leukemia virus (MuLV) and HIV. HIV is the virus known to cause acquired immunodeficiency syndrome (AIDS) in humans and AIDS presents special problems to the medical community which the present invention addresses.

BACKGROUND OF THE INVENTION

Modern medical science is constantly searching for new and more powerful agents to prevent, treat or retard bacterial and viral infections and cure the diseases they cause. Bacterial and viral infections of humans and domestic animals cost billions of dollars annually. Vast sums of money are spent each year by pharmaceutical companies to identify, characterize, and produce new antibiotics and antivirals to combat the emerging drug resistant strains which have become a serious problem. Reliable prophylactic treatments for disease prevention are also of major interest. Yet, despite the costs and efforts to identify treatments for viral infections, such as hepatitis and AIDS, effective therapies remain elusive.

Hepatitis is a disease of the human liver. It is manifested with inflammation of the liver and is usually caused by viral infections and sometimes from toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious. HBV is a DNA virus with a virion size of 42 nm. HCV is a RNA virus with a virion size of 30–60 nm. See D. S. Chen, J. Formos. Med. Assoc., 95(1), 6–12 (1996).

Hepatitis B is a major health problem worldwide, especially in Asia and Africa. Approximately 300 million people are chronically infected with HBV worldwide. More than one million carriers of HBV are found in the United States and HBV infection is currently the main cause of liver cirrhosis and cancer. HBV carriers not only become long-term reservoirs of the virus but also may develop chronic liver disease and have a greatly increased risk of developing liver cirrhosis and cancer. The progression from chronic hepatitis B to cirrhosis is frequently insidious and occurs without a noticeable change in symptoms. Once the symptoms of cirrhosis or cancer are manifested, therapies are of little value.

Current prevention of HBV infection is a hepatitis B vaccination which is safe and effective. However, vaccination is not effective in treating those already infected (i.e., carriers and patients). Many drugs have been used in treating chronic hepatitis B and none have been proven to be effective, except interferon. Treatment with interferon has limited success and has frequently associated adverse side effects such as fatigue, fever, chills, headache, myalgias, arthralgias, mild alopecia, psychiatric effects and associated disorders, autoimmune phenomena and associated disorders and thyroid dysfunction. Treatment with interferon for sixteen (16) weeks has been shown to be effective with a sustained loss of viral replication in approximately 40% of hepatitis B patients. The great majority of responders had normal serum aminotransferase levels and relapse rates appear to be low. See R. P. Perrillo, Digestive Diseases and Sciences, 38(4), 577–593 (1993). However, a higher long-term relapse rate (24%) was reported in Chinese patients with chronic hepatitis B who underwent interferon therapy. See A. S. F. Lok, H. T. Chung, V. W. S. Liu, & O. C. K. Ma, Gastroenterology, 105(6), 1833–1838 (1993).

Moreover, serum hepatitis B surface antigen (HBsAg) disappeared in 10–15% of patients treated with interferon. The loss of HBsAg coincided with the disappearance of HBV. Improvement in liver histology was sustained years later in HBsAg-negative patients. The lack of disease progression could thus conceivably result in the prevention of liver cancer when treatment is provided in the pre-cirrhotic stage of infection. See R. P. Perrillo, Digestive Diseases and Sciences, 38(4), 577–593 (1993).

Hepatitis C has been previously described as a non-A non-B hepatitis, which is caused by HCV. There are approximately 100 million HCV carriers worldwide. An estimated 3.5 million people have chronic hepatitis C in the United States. HCV infection will lead to liver cirrhosis and cancer with less clinical manifestation. Most hepatitis C patients do not have particular symptoms and can thus be easily overlooked until it is too late for therapy. This poses a potentially more serious problem than hepatitis B. HCV carriers also become long-term reservoirs of the virus and eventually develop chronic liver disease and have a greatly increased risk of developing liver cirrhosis and cancer. See D. S. Chen, Science, 262, 369–370 (1993).

No effective immunization is currently available, and hepatitis C can only be controlled by other preventive measures such as improvement in hygiene and sanitary conditions and interrupting the route of transmission. At present, the only acceptable treatment for chronic hepatitis C is interferon which requires at least six (6) months of treatment. Treatment with interferon has limited long term efficacy with a response rate about 25%. Initial treatment has a response rate of about 50% however, half of those which respond relapse after cessation of interferon treatment. Therefore, only about 25% of patients had a sustained response. See D. S. Chen, J. Formos. Med. Assoc., 95(1), 6–12 (1996) and N. Terrault & T. Wright, New Engl. J. Med., 332(22), 1509–1511 (1995).

Because the interferon therapy has limited efficacy and frequent adverse effects, a more effective regimen is needed.

New antivirals and immune modulators are presently undergoing clinical trials.

AIDS is a deadly disease of an acquired immunodeficiency syndrome in humans caused by HIV. It has been plaguing the world since the first description of the disease in 1981 and the discovery of its causative agent, HIV, in 1983. About 13 million people were infected with HIV worldwide in 1993 and the number has increased to about 21 million in 1996. See B. Jasny, Science, 260(5112), 1219 (1993) and P. Piot, Science, 272(5270), 1855 (1996).

Several drugs have been approved for treatment of this devastating disease, including azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). See M. I. Johnston & D. F. Hoth, Science, 260(5112), 1286–1293 (1993) and D. D. Richman, Science, 272(5270), 1886–1888 (1996).

All drugs currently approved for AIDS treatment utilize inhibition of viral proliferation and are viral reverse transcriptase inhibitors or viral protease inhibitors. More protease inhibitors, such as nelfinavir and improved saquinavir, are in development. An AIDS vaccine (Salk's vaccine) has been tested and several proteins which are chemokines from CD8 have been discovered to act as HIV suppressors.

In addition to the above synthetic nucleoside analogs, proteins, and antibodies, several plants and substances derived from plants have been found to have in vitro anti-HIV activity, such as *Lonicera japonica* and *Prunella vulgaris*, and glycyrrhizin from *Glycyrrhiza radix*. See R. S. Chang & H. W. Yeung, Antiviral Research, 9, 163–175 (1988) and M. Ito, et al., Antiviral Research, 7, 127–137 (1987).

Despite all of the available pharmaceuticals for the treatment of HIV, there is still no cure for the deadly disease. HIV viruses continue to mutate and become resistant to existing drugs such as the reverse transcriptase inhibitors and protease inhibitors. Recently, a therapy of using two (2) or three (3) anti-HIV drugs in combination has been found effective in significantly lowering the HIV loads in AIDS patients. The results have been promising, however the virus continues to develop resistance to the drugs and the long-term outcome (survival and cure rates) is still unknown. Thus, the medical communities throughout the world continue to search for drugs that can prevent HIV infections, treat HIV carriers to prevent them from progressing to full-blown deadly AIDS, and treat the AIDS patient.

The use of herbal drugs and folk medicines have been known for thousands of years in China. These herbal approaches to the treatment of numerous illnesses, from arthritis to viral infections, have been viewed by western modern medicine as ineffective and dangerous. Records of the use of herbs date from ancient China, Egypt and Biblical times. Early physicians used hundreds of herbs to treat a variety of ailments. The practice is still widespread, especially in Asia and Europe. During the 19th century, many home remedies containing herbs were patented and sold. Modern drugs have replaced those remedies, but many modern drugs contain ingredients derived from herbs.

In 1776, the English botanist and physician William Withering learned that an herbal tea made by an old farm woman was effective in treating dropsy, or excess water in the tissues, which is caused by the inability of the heart to pump strongly enough. He found that one ingredient of the tea, which was made with leaves of the foxglove plant, strengthened the heart's pumping ability. The drug made from the foxglove plant is now known as digitalis.

Folk medicine is a relatively modern term to the West and has come to mean the care and treatment of the sick through a variety of herbal medicines. In recent years, folk medicines have become of increasing interest to many people in the western scientific medical community.

PRIOR ART

A Chinese herbal medicine known as AEGINETIAE HERBA (a.k.a. GOLDEN LOCK KEY or LOTUS HERBA); has traditionally been used to treat illnesses such as swollen and sore throat, urinary tract infection, osteomyelitis, boils, tonsillitis, goiter, pharyngitis, thyroiditis, enteritis, liver disease, cancer, rheumatism, hematemesis, neurasthenia, eye redness, piles, menstruation irregularity, dropsy, jaundice, hernia, snake bite, and child developmental retardation. AEGINETIAE HERBA is prepared from the dried whole plant of *Aeginetia indica* which belongs to the family Orobanchaceae *Dichondra micrantha, Striga lutea* and *Dichondra repens* are also used to prepare this herbal medicine. Treatment dosage using the dried plant is typically from 4 to 150 g per day. It should be noted that the plant tastes bitter and is toxic.

Okubo et al. disclose that a phosphate buffered saline (PBS) extract (pH 7.2 at ambient to 4° C.) from the seeds of *Aeginetia indica* exhibits excellent carcinostatic effect and possesses interleukin-2 and interferon-$\gamma$ inducing properties. The PBS was a 0.1M phosphate buffered physiological saline at pH 7.2, not containing calcium or magnesium ions. The extracted substance is taught to be a macromolecular polysaccharide which may or may not contain lipid A binding with protein depending on whether the extraction is conducted using butanol or phenol. The extracted substance was soluble in water and insoluble in n-butanol. Its molecular weight was within the range of 100,000 to 200,000 Dalton. See S. Okubo, M. Sato, & K. Himeno, U.S. Pat. No. 5,366,725, issued on Nov. 22, 1994.

A Chinese herbal medicine known as BAPHICACANTHIS RHIZOMA ET RADIX has traditionally been used to treat illnesses such as fever, abscesses, erysipelas, swollen sore throat, hematemesis, epistaxis, typhus, typhoid, mumps, puerperal fever, flu, measles, beriberi, headache, jaundice, plague, leucorrhea, and syphilis. BAPHICACANTHIS RHIZOMA ET RADIX is prepared from the dried rhizoma and root of *Baphicacanthes cusia, Strobilanthes cusia, Isatis tinctoria, Isatis indigotica,* or *Polygonum tinctorium*. It has been reported that this herbal medicine has exhibited inhibition of flu virus in vitro. Aqueous extracts from boiling the root of *Isatis tinctoria* have also exhibited antibacterial effect.

The dried leaf of *Baphicacanthes cusia, Isatis tinctoria, Isatis indigotica,* or *Polygonum tinctorium* have been used to prepare another herbal medicine known as BAPHICACANTHIS FOLIUM. BAPHICACANTHIS FOLIUM has traditionally been used to treat illnesses such as typhus, typhoid, measles, fever, erysipelas, sore throat, tonsillitis, dysentery, acute laryngitis, stomatitis, gum bleeding, and various infectious diseases with fever. It has also exhibited antibacterial effects and antipyretic effects. The leaf of *Isatis tinctoria* has been used as an antipyretic in the past.

The leaf of *Baphicacanthes cusia, Isatis tinctoria, Isatis indigotica,* or *Polygonum tinctorium* with additional processing has also been used to prepare a third related herbal medicine known as INDIGO PULVERATA LEVIS. INDIGO PULVERATA LEVIS has traditionally been used to treat illnesses such as epistaxis, rashes, sores, mumps, chronic skin boils, dermatitis, anemia, fever, swollen sores, stomatitis, acute laryngitis, tonsillitis, gingivitis, parasitic oral mucosa inflammation, snake or dog bites, malignant sores, and erysipelas. Ethanol extracts of INDIGO PULVERATA LEVIS have exhibited bacterial inhibition properties.

Baphicacanthes cusia and Strobilanthes cusia belong to the family of Acanthaceae. Isatis tinctoria and Isatis indigotica belong to the family of Cruciferae. Polygonum tinctorium belongs to the family of Polygonaceae. BAPHICACANTHIS RHIZOMA ET RADIX tastes bitter while BAPHICACANTHIS FOLIUM tastes bitter and salty, and is nontoxic. INDIGO PULVERATA LEVIS tastes salty and is also nontoxic. Treatment doses are typically 10 to 19 g per day for BAPHICACANTHIS RHIZOMA ET RADIX, 8 to 30 g per day for BAPHICACANTHIS FOLIUM, and 0.4–1.1 g per day for INDIGO PULVERATA LEVIS.

Ho et al. disclose the use of an extract from a mixture of herbs for the in vitro inhibition of HIV infection in human T lymphocyte cells and mononuclear phagocytic lineage cells. The activity was based on the test results of a water extract from a mixture of three herbs: Isatis tinctoria (or Isatis indigotica), Lonicera japonica, and Polygonum bistorta. See D. D. Ho & X. S. Li, U.S. Pat. No. 5,178,865, issued on Jan. 12, 1993.

The compound known as tryptanthrin has been identified as the principal antifungal agent in the leaf of Strobilanthes cusia and as the main antidermatophytic substance in the leaf of Polygonum tinctorium and Isatis tinctoria. See H. Y. Hsu, Y. P. Chen, & M. Hong, The Chemical Constituents Of Oriental Herbs, Vol. 2, Oriental Healing Arts Institute, Los Angeles, Calif., U.S.A., 758–759 (1985).

A Chinese herbal medicine known as BLECHNI RHIZOMA or DRYOPTERIS CRASSIRHIZOMAE RHIZOMA has traditionally been used to treat conditions such as cuts, swelling, fever, measles, hematemesis, menorrhagia, dysentery, stool with traces of blood, abdominal pain caused by parasites, wound bleeding, uterus bleeding, puerperal abdominal pain, and erysipelas. BLECHNI RHIZOMA is prepared from the dried root and stem of Blechnum orientate which belongs to the family of Polypodiaceae or Blechnaceae. DRYOPTERIS CRASSIRHIZOMAE RHIZOMA is prepared from the dried root and stem of Dryopteris crassirhizoma which belongs to the family of Aspidiaceae. Osmunda japonica(Osmundaceae family), Woodwardia orientalis and Woodwardia unigemmata (Blechnaceae family), Athyrium acrostichoides (Aspidiaceae or Athyriaceae family), Sphaeropteris lepifera (Cyatheaceae family), Cyrtomium falcatum, and Cyrtomium fortunei (Aspidiaceae family) have also been used for preparation of the herbal medicines. These herbal medicines taste bitter and astringent, and are slightly toxic. Treatment dosage is typically 4–11 g per day.

The sprout of Blechnum orientate has been used to treat swelling while the sprouts of Sphaeropteris lepifera (also known as (hereinafter "a.k.a.", Alsophila pustulosa) have been used to treat carbuncles. Blechnum orientate has also shown a strong inhibition effect against the influenza virus. Filmarone, filicin, aspidin, albaspidin, and filicic acid which are found in Dryopteris crassirhizoma have been characterized as having an anthelmintic effect. See H. Y. Hsu, Y. P. Chen, S. G. Hsu, J. S. Hsu, C. J. Chen, & H. C. Chang, Concise Pharmacognosy, New Medicine Publishing Co., Taipei, R.O.C., 577–578 (1985); and H. Y. Hsu, Y. P. Chen, & M. Hong, The Chemical Constituents Of Oriental Herbs, Oriental Healing Arts Institute, Los Angeles, Calif., U.S.A., 249–250 (1982).

Hozumi et al. disclosed that the rhizome of Dryopteris crassirhizoma was an antiherpesviral agent, antipolioviral agent, and anti-varicella-zoster virus agent. The rhizome of Cyrtomium fortunei and the rhizome of Woodwardia orientalis were also disclosed as antiherpesviral, antipolioviral, anti-measles virus, anti-varicella-zoster virus, anti-cytomegalovirus (CMV), and an anti-DNA and anti-RNA virus agents. See T. Hozumi, T. Matsumoto, H. Ooyama, T. Namba, K. Shiraki, M. Hattori, M. Kurokawa, & S. Kadota, U.S. Pat. No. 5,411,733, issued May 2, 1995.

A Chinese herbal medicine known as BLETILLAE TUBER has traditionally been used to treat illnesses such as hemoptysis, epistaxis, hematemesis, abscesses, burns, dry and chapped skin, tuberculosis, gastric ulcers, and sores. BLETILLAE TUBER has astringent, antibacterial and antifungal properties. BLETILLAE TUBER is prepared from the dried tuber of Bletilla striata which belongs to the family of Orchidaceae. BLETILLAE TUBER tastes bittersweet, astringent and is nontoxic. Treatment dose is typically 2–11 g per day for an average human.

Bletilla-glucomannan is a mucilage in the tuber of Bletilla striata which has astringent properties (can be used to stop bleeding and decrease swelling). See H. Y. Hsu, Y. P. Chen, S. G. Hsu, J. S. Hsu, C. J. Chen, & H. C. Chang, Concise Pharmacognosy, New Medicine Publishing Co., Taipei, R.O.C., 381 (1985); and H. Y. Hsu, Y. P. Chen, & M. Hong, The Chemical Constituents Of Oriental Herbs, Oriental Healing Arts Institute, Los Angeles, Calif., U.S.A., 114–115 (1982).

Chinese herbal medicines known as CIRSII RHIZOMA ET RADIX and BREEAE RADIX have traditionally been used to treat illnesses such as hematemesis, urine with traces of blood, stool with traces of blood, gonorrhea with traces of blood, menorrhagia, leucorrhoea, boils, acute infectious hepatitis, cuts, bleeding sores, and abscesses. CIRSII RHIZOMA ET RADIX is prepared from the dried rhizoma or root or the whole plant of plants such as Cirsium japonicum, Cirsium albescens, and Cirsium japonicum var. australe which are from the Compositae family. BREEAE RADIX is prepared from the dried root of Compositae family plants such as Breea segetum (a.k.a., Cephalanoplos segetum) and Breea setosum. Both herbal medicines taste sweet and slightly bitter, and are nontoxic. Treatment dose is typically 5 to 75 g per day for the average human.

A Chinese herbal medicine known as FORSYTHIAE FRUCTUS has traditionally been used to treat illnesses such as sores, abscesses, lymph node swelling, neck lymph node tuberculosis, erysipelas, gonorrhea, measles, ecchymosis, urethritis, and hypertension. It was also found to inhibit several bacteria and influenza viruses. FORSYTHIAE FRUCTUS is prepared from the dried mature fruit of Forsythia suspensa, Forsythia viridissima, or Forsythia koreana which belong to the family Oleaceae. The herbal medicine tastes bitter and is nontoxic. Treatment dosage is typically 3 to 11 g per day.

Hozumi et al. disclose that the fruit of Forsythia suspensa is an antipolioviral agent and an anti-measles virus agent useful in treating these viral infections. See T. Hozumi, T. Matsumoto, H. Ooyama, T. Namba, K. Shiraki, M. Hattori, M. Kurokawa, & S. Kadota, U.S. Pat. No. 5,411,733, issued May 2, 1995.

The compounds Forsythoside A (found in the leaf of Forsythia suspensa), forsythoside B (found in the stem of Forsythia koreana), forsythoside C and forsythoside D (found in the fruit of Forsythia suspensa) have been reported to exhibit antibacterial activity against Staphylococcus

*aureus* at a concentration less than 2 mM. Suspensaside (found in the fruit of Forsythia suspensa, likely the same as forsythoside C) has also been reported to exhibit antibacterial activity against *Staphylococcus aureus* Terashima with a minimum inhibition concentration (MIC) of 2.6 mg/mL. See H. Y. Hsu, Y. P. Chen, & M. Hong, The Chemical Constituents Of Oriental Herbs, Vol. 2, Oriental Healing Arts Institute, Los Angeles, Calif., U.S.A., 53–55, 142–143 (1985).

A Chinese herbal medicine known as HEDYOTIS (a.k.a., OLDENLANDIAE HERBA) has traditionally been used to treat illnesses such as malignant swelling, urethra infection, pharyngitis, laryngitis, tonsillitis, toxic snake bites, subacute or chronic coccygodynia, prurigo, carbuncle, appendicitis, intestinal cancer, contusion injuries and eye diseases. It has also been found to have weak antibacterial activity in vitro. HEDYOTIS is prepared from the dried whole plant of *Hedyotis diffusa* (a.k.a., *Oldenlandia diffusa*) which belongs to the family Rubiaceae. The herbal medicine tastes sweet and is nontoxic. Treatment dosage is typically 19 to 300 g per day.

The Chinese herbal medicines known as LESPEDEZAE HERBA and SENECINIS HERBA have traditionally been used to treat illnesses such as urine incontinence, gonorrhea, leucorrhoea, asthma, stomach ache, general weakening and exhaustion, a children's disease characterized by swelling of the belly and limbs caused by malnutrition or parasitic worms, diarrhea, contusion injuries, eye diseases, visual impairment, eye redness, renal disease, breast abscess, acute inflammatory disease, cataracts, dysentery, enteritis, jaundice, flu, septicemia, abscesses, boils, ringworm, erysipelas, snake or dog bites, rheumatic pains, sores, swelling and a disease of the palm. LESPEDEZAE HERBA is prepared from the dried whole plant of *Lespedeza cuneata* which belongs to the family Leguminosae. SENECINIS HERBA is prepared from the dried whole plant of *Senecio scandens* which belongs to the family Compositae. The extracts of *Lespedeza cuneata* and *Senecio scandens* have been shown to have antibacterial effects. Both herbs taste sour, astringent and bitter. Treatment dose is typically 4 to 40 g per day.

A Chinese herbal medicine known as LIGUSTRI FRUCTUS has traditionally been used as a tonic and to treat illnesses such as debility, knee limpness, tinnitus and dizziness, palpitation, insomnia, constipation, early white hair, neck lymph node, tuberculosis, lung tuberculosis, intermittent fever and dropsy. LIGUSTRI FRUCTUS is prepared from the dried mature fruit of *Ligustrum lucidum* or *Ligustrum japonicum* which belongs to the family Oleaceae. The leaves of *Ligustrum lucidum* have been used as an antipyretics, analgesics and anti-inflammatory agents. The leaves of *Ligustrum japonicum* have also been used to treat illnesses such as ophthalmalgia, ulcerative stomatitis, mastitis, swelling, and burns. The fruit of *Ligustrum lucidum* taste bitter and are nontoxic. Typical treatment dosage of the dried fruit is typically 6 to 20 g per day. That of the dried leaves is typically 40 to 75 g per day.

A Chinese herbal medicine known as LONICERAE FLOS has traditionally been used to treat illnesses such as fever, febrile diseases, acute infectious diseases, measles, carbuncle, dysentery, malignant sores and swelling, abscesses, boils, gonorrhea, syphilis, poisoning, enteritis, swelling, ringworm and similar skin diseases. LONICERAE FLOS is prepared from the dried flower bud of *Lonicera japonica* or *Lonicera confusa*. Both plants belong to the family Caprifoliaceae. The flower of *Lonicera japonica* has diuretic, antipyretic, anti-inflammatory, anti-convulsive, antibacterial and antiviral properties. The flower bud has also been used as a diuretic. The herbal medicine tastes sweet and is nontoxic. Treatment dosage is typically 11 to 75 g per day for the typical human.

The dried vine, stem and leaf of *Lonicera japonica* is used for preparation of another herbal medicine called LONICERAE CAULIS ET FOLIUM, which has traditionally been used to treat illnesses such as paralysis and pain caused by rheumatism, rheumatism swelling, rheumatic pain, carbuncle swelling, arthritis, gonorrhea, enteritis, and various symptoms with pus, such as abscesses. Extracts have exhibited the ability to raise blood sugar levels in rabbits. The root of *Lonicera japonica* has also been used to treat illnesses such as venereal disease, syphilis, gonorrhea, lymph node tuberculosis, contusion injury, and skin disease. Treatment doses are typically 8 to 75 g per day for the stem or leaf and 110 to 150 g per day for the root.

Ho et al. disclose the anti-HIV activity in vitro of a mixture *Lonicera japonica*, *Isatis tinctoria* (or *Isatis indigotica*) and *Polygonum bistorta* or a mixture of *Lonicera japonica* with *Scutellaria baicalensis*. Water extractions of the mixtures, treatment with ethanol for precipitation and charcoal adsorption are disclosed for the preparation for the anti-HIV active composition. See D. D. Ho & X. S. Li, U.S. Pat. No. 5,178,865, issued on Jan. 12, 1993. Several tannins such as caffeoylquinates isolated from *Lonicera japonica* have been reported to have an inhibitory effect on HIV-1 reverse transcriptase activity. See C. W. Chang, M. T. Lin, S. S. Lee, K. C. S. C. Liu, F. L. Hsu, & J. Y. Lin, Antiviral Research, 27(4), 367–374 (1995).

A mixture of aqueous extracts of *Lonicera japonica* flower buds and *Forsythia suspensa* fruits with the crude flavonoids from *Scutellaria baicalensis* have been shown to have antibacterial and antiviral properties. A group of patients with severe respiratory disease were treated with the mixture and they responded as well as a control group on standard antibiotic therapy. See P. J. Houghton, Z. Boxu, & Z. Xisheng, Phytother. Res., 7(5), 384–386 (1993).

A Chinese herbal preparation which consisted of ten (10) herbs such as *Prunus armeniacae*, *Scutelaria baicalensis*, *Lonicera japonica*, etc. was shown to have strong inhibitory effects in vitro against *Streptococcus hemolyticus*, *Staphylococcus aureus*, Flexners *Dysentery bacillus*, *Diplococcus pneumoniae* and *Pseudomonas aeruginosa*. The preparation was shown to be as effective as penicillin and aminophylline in treating bronchopneumonia and acute bronchitis patients. See Y. Q. Li, W. Yuan, & S. L. Zhang, Chung Kuo Chung Hsi I Chieh Ho Tsa Chih, 12(12), 708, 719–721, 737 (1992).

Another Chinese herbal preparation which consisted of *Lonicera japonica*, *Ophiopogon japonicus*, and *Astragalus membranaceus* was shown to be effective in treating viral myocarditis. The authors reported that the preparation could directly inactivate the virus of Coxsackie B3, protect heart cells in mice, prevent attack by Coxsackie B3, promote the production of interferon and increase the functionality of NK cells to regulate immunity in experimental mice. See H. J. Yan, Chung Hsi I Chieh Ho Tsa Chih, 11(8), 452, 468–470 (1991).

A Chinese herbal medicine known as PHELLODENDRI CORTEX has traditionally been used to treat illnesses such as dysentery, diarrhea, jaundice, stools with blood, piles, tinnitus, mouth and tongue boils, abscesses, sores, leucorrhea with blood, abdominal pain, indigestion, bacteroid enteritis, and tuberculoid diarrhea. The herbal medicine has also been used as an eye wash, for strengthening stomach and intestine, stimulate appetite, and as an astringent, anti-inflammatory, etc. It has antibacterial, anti-inflammatory, and wound healing properties. PHELLODENDRI CORTEX is prepared from the dried cortex of plants from the Rutaceae family such as *Phellodendron amurense, Phellodendron chinense, Phellodendron amurense* var. *sachalinense,* and *Phellodendron wilsonii.* PHELLODENDRI CORTEX tastes bitter and is nontoxic. Treatment dose is typically 1 to 11 g per day.

Hozumi et al. disclose the bark of *Phellodendron amurense* as an antiherpesviral, antipolioviral, anti-measles virus, anti-varicella-zoster virus, anti-CMV and anti-DNA virus and anti-RNA virus agents. See T. Hozumi, T. Matsumoto, H. Ooyama, T. Namba, K. Shiraki, M. Hattori, M. Kurokawa, & S. Kadota, U.S. Pat. No. 5,411,733, issued on May 2, 1995.

A Chinese herbal medicine known as POLYGONI CUSPIDATI RHIZOMA has traditionally been used to treat illnesses such as dysentery, leucorrhea, fever, headache, menorrhagia, dysmenorrhea, breast abscesses, sores, boils, contusion injury, menstruation irregularity, puerperal ecchymotic abdominal distension and pain, dysuria, infantile growth and appendicitis. POLYGONI CUSPIDATI RHIZOMA is prepared from the dried rhizoma of *Polygonum cuspidatum, Polygonum runcinatum,* or *Polygonum reynoutria* (a.k.a. *Reynoutria japonica*) which belong to the family Polygonaceae. The tender leaf has also been used to treat contusion and cut injuries. Extracts of the herbal medicine have exhibited antibacterial and antiviral effects in vitro. Excessive use of the herbal medicine may cause a slight diarrhea. The herbal medicine tastes bitter and the treatment dose is typically 6 to 40 g per day.

Hozumi et al. disclose the root and rhizome of *Polygonum cuspidatum* as an antiherpesviral, antipolioviral, anti-varicella-zoster virus, and anti-CMV agent. See T. Hozumi, T. Matsumoto, H. Ooyama, T. Namba, K. Shiraki, M. Hattori, M. Kurokawa, & S. Kadota, U.S. Pat. No. 5,411,733, issued on May 2, 1995.

Resveratrol has also been reported as an antifungal and antibacterial component in the root of *Polygonum cuspidatum.* See H. Y. Hsu, Y. P. Chen, & M. Hong, The Chemical Constituents Of Oriental Herbs, Vol. 2, Oriental Healing Arts Institute, Los Angeles, Calif., U.S.A., 51 (1985).

A Chinese herbal medicine known as PRUNELLAE SPICA has traditionally been used to treat illnesses such as goiter, scrofula, neck lymph node tuberculosis, lymph node swelling, eye redness, pain, abscesses, sores, hemorrhoids, swollen eye, ophthalmalgia, leucorrhoea with traces of blood, gonorrhea, uterine disease, mastitis, breast abscesses, breast cancer, foot swelling, paralysis, chronic arthritis, conjunctivitis, and hypertension. PRUNELLAE SPICA is prepared from the dried spica or whole plant of *Prunella vulgaris* or *Prunella vulgaris* subsp. *asiatica* (a.k.a., *Prunella vulgaris* var. *lilachina*). Both plants belong to the family Labiatae. The whole plant can be used as a diuretic and also has antibacterial effects in vitro. The herbal medicine tastes bitter and is nontoxic. Treatment dosage is typically 4 to 110 g per day for the average human.

Hozumi et al. disclose that the spike of *Prunella vulgaris* as an antiherpesviral agent for treating herpes virus infection. See T. Hozumi, T. Matsumoto, H. Ooyama, T. Namba, K. Shiraki, M. Hattori, M. Kurokawa, & S. Kadota, U.S. Pat. No. 5,411,733, issued May 2, 1995. The water extract of *Prunella vulgaris* (boiling 3 g in 100 mL water for 45 minutes) was also reported to have anti-HIV (strain H9/3B) activity. The extract also exhibited synergistic anti-HIV activity with zidovudine (AZT) and didanosine (ddI). Only a slight additive effect was observed for *Prunella vulgaris* and zalcitabine (ddC). See J. F. John, R. Kuk, & A. Rosenthal, Abstr. Gen. Meet. Am. Soc. Microbiol., 94, 481 (1994).

Yamasaki et al. evaluate in vitro, two hundred and four (204) crude drugs of common use in Japan for anti-HIV-1 activity and reported that the hot water extract of *Prunella vulgaris* (spike) showed a strong in vitro anti-HIV-1 activity with an $IC_{100}$ of 16 $\mu$g/mL. See K. Yamasaki, T. Otake, H. Mori, M. Morimoto, N. Ueba, Y. Kurokawa, K. Shiota, & T. Yuge, Yakugaku Zasshi, 113(11), 818–824 (1993).

Yao et al. report that the water extract of the dried entire plant of *Prunella vulgaris* was active in vitro in inhibiting HIV-1 replication with relatively low cytotoxicity towards the MT-4 cells. The extract was also active in reverse transcriptase inhibition. The active factor was purified and identified as anionic with a molecular weight of approximately 10,000 Dalton. This active component may be the same as the prunellin, as described below by Tabba et al. The purified extract inhibited HIV-1 replication in the lymphoid cell line MT-4, in the monocytoid cell line U937, and in peripheral blood mononuclear cells (PBMC) at effective concentrations of 6, 30, and 12.5 $\mu$g/mL, respectively. Pretreatment of uninfected cells with the extract prior to viral exposure did not prevent HIV-1 infection. Preincubation of HIV-1 with the purified extract dramatically decreased infectiousness. The purified extract was also able to block cell-to-cell transmission of HIV-1, prevented syncytium formation, and interfered with the ability of both HIV-1 and purified gp120 to bind to CD4. PCR (polymerase chain reaction) analysis confirmed the absence of HIV-1 proviral DNA in cells exposed to virus in the presence of the extract. The results suggested that the purified extract antagonized HIV-1 infection of susceptible cells by preventing viral attachment to the CD4 receptor. See X. J. Yao, M. A. Wainberg, & M. A. Parniak, Virology, 187(1), 56–62 (1992).

Tabba et al. isolated and partially characterized an anti-HIV component, prunellin, from aqueous extracts of *Prunella vulgaris.* Prunellin is a carbohydrate with an MIC (minimum inhibition concentration) of 2.2 $\mu$g/mL against HIV-1 in vitro. It was identified as a partially sulfated polysaccharide with a molecular weight of about 10,000 Dalton. See H. D. Tabba, R. S. Chang, & K. M. Smith, Antiviral Research, 11, 263–273 (1989).

Zheng evaluated four hundred seventy two (472) traditional medicinal herbs for antiviral effect on type 1 herpes simplex virus (HSV1). *Prunella vulgaris* was one of the ten herbs found to be highly effective in vitro. Clinically, 78 cases of herpetic keratitis due to HSV1 were treated with *Prunella vulgaris* and *Pyrrosia lingua* eye drops. Among them, 38 cases were effectively cured, 37 cases showed an improvement, and 3 cases showed no benefit. See M. Zheng, J. Tradit. Chin. Med., 8(3), 203–206 (1988).

Triterpene 1 and Triterpene 2 which have been isolated from *Prunella vulgaris* have shown antiviral activity against HSV1. Triterpene 1 was identified as betulinic acid and triterpene 2 was identified as 2$\alpha$,3$\alpha$-dihydroxyurs-12-en-28-oic acid. The $EC_{50}$ was estimated to be 30 $\mu$g/mL for triterpene 1 and 8 $\mu$g/mL for triterpene 2 by plaque reduction assay. See S. Y. Ryu, C-K. Lee, C. O. Lee, H. S. Kim, & O. P. Zee, Arch. Pharmacal Res. (Seoul), 15(3), 242–245 (1992).

A Chinese herbal medicine known as SCUTELLARIAE BARBATAE HERBA has traditionally been used to treat illnesses such as hematemesis, gonorrhea with traces of blood, jaundice, sore throats, lung abscesses, boils, carbuncles, abscesses, neck lymph node swelling, sores, cancer, contusion or cut injuries, snake bite injuries, dysentery with traces of blood, convulsions, pneumonia, abdominal pains, congenital diseases, enteritis, coccygodynia, appendicitis, asthma, malaria, and rheumatism. It was also found to have antibacterial effect. SCUTELLARIAE BARBATAE HERBA is prepared from the dried whole plant of *Scutellaria barbata, Scutellaria rivularis,* or *Scutellaria dependens* which belong to the family Labiatae. The herbal medicine tastes bitter and should not be consumed by those who have anemia. Pregnant women should avoid taking this herb. Treatment dosage is typically 4 to 300 g per day.

Dried whole plants of *Scutellaria rivularis* have been used in folk medicine for the treatment of tumors, hepatitis, liver cirrhosis, and other diseases in China and Taiwan. See Y. L. Lin, Y. H. Kuo, G. H. Lee, and S. M. Peng, J. Chem. Research (S), 320–321.(1987).

Apigenin, isolated from the whole herb of *Scutellaria rivularis,* was found to have anti-influenza virus activity. See T. Nagai, et al., Chem. Pharm. Bull., 38(5), 1329–1332 (1990).

A Chinese herbal medicine known as SOLANI HERBA has traditionally been used to treat illnesses such as boils, abscesses, erysipelas, contusion or sprain injuries, chronic bronchitis, acute nephritis, cancer, swelling, hernia, ulcers, carbuncles with swelling and sores. SOLANI HERBA is prepared from the dried whole plant of *Solanum nigrum* which belongs to the family Solanaceae. Extracts of SOLANI HERBA have demonstrated anti-inflammatory properties. The fruit has also exhibited the effects of suppressing coughs and relieving bronchial inflammation. The herbal medicine tastes bitter and slightly sweet and is nontoxic. Treatment dosage is typically 11 to 60 g per day.

The root of *Solanum nigrum* was believed to have antipyretic activity and has been used for treating high fevers by some primitive tribes of western Ghats in India. A decoction prepared from *Solanum nigrum* plants, *Glycosmis Mauritania* seeds and/or *Santalum album* wood chips was believed to have expectorant activity and has been used for coughs and to treat hemoptysis. See P. Pushpangadan and C. K. Atal, J. Ethnopharmacol., 11(1), 59–77 (1984).

The compound solasonine (found in the whole herb, fruit, leaf, and fresh immature berries of *Solanum nigrum*) has an anti-inflammatory effect similar to cortisone. Solasonine and solanine (also found in *Solanum nigrum*) possesses the ability of raising or lowering the blood sugar level in rats depending on the situation of the animals. Solasonine was also reported to have a stimulating effect on the heart, while solanine had a suppressive effect. When administered at small doses, solasonine enhances the stimulative process of the central nerve system in animals (i.e., rat and rabbit). On the other hand, it enhances the suppressive process when administered at large doses. Solasonine can also lower the blood coagulability. See (1) H. Y. Hsu, Y. P. Chen, S. G. Hsu, J. S. Hsu, C. J. Chen, & H. C. Chang, Concise Pharmacognosy, New Medicine Publishing Co., Taipei, R.O.C., 176–177 (1985); (2) H. Y. Hsu, Y. P. Chen, & M. Hong, The Chemical Constituents Of Oriental Herbs, Oriental Healing Arts Institute, Los Angeles, Calif., U.S.A., 1400–1401, 1406 (1982); and (3) H. Y. Hsu, Y. P. Chen, & M. Hong, The Chemical Constituents Of Oriental Herbs, Vol. 2, Oriental Healing Arts Institute, Los Angeles, Calif., U.S.A., 742 (1985).

Additionally, Yamasaki et al. report that the hot water extract of *Lithospermum erythrorhizon* (root) showed a strong in vitro anti-HIV-1 activity with an $IC_{100}$ of 16 µg/mL. Yao et al. reported that the water extracts of the dried root of *Arctium lappa* and the dried aerial parts of *Andrographis paniculata* were anti-HIV-1 active in vitro and cytotoxic towards the MT-4 cells. Both extracts were also active in reverse transcriptase inhibition. See K. Yamasaki, T. Otake, H. Mori, M. Morimoto, N. Ueba, Y. Kurokawa, K. Shiota, & T. Yuge, Yakugaku Zasshi, 113(11), 818–824 (1993); and X. J. Yao, M. A. Wainberg, & M. A. Parniak, Virology, 187(1), 56–62 (1992).

Glycyrrhizin is reported to have an inhibitory effect on the in vitro infectivity and cytopathic activity of HIV. See M. Ito, et al, Antiviral Research, 7, 127–137 (1987). Glycyrrhizin is a saponin found in the herbal medicine GLYCYRRHIZAE RADIX. GLYCYRRHIZAE RADIX is prepared from the dried root of *Glycyrrhiza uralensis, Glycyrrhiza glandulifera, Glycyrrhiza echinata,* or *Glycyrrhiza glabra* all of which belong to the family Leguminosae.

Chang and Yeung screened the boiling water extracts of twenty seven (27) medicinal herbs for anti-HIV activity. They found eleven (11) of the extracts were active in inhibiting HIV in the H9 cells. *Lonicera japonica, Prunella vulgaris, Woodwardia unigemmata,* and *Senecio scandens* were among those active ones with moderate activities. *Forsythia suspensa, Isatis tinctoria,* and *Polygonum cuspidatum* were among those tested which did not display activity in the anti-HIV assay. The anti-HIV active extract of *Viola yedoensis* was further tested and found to be fairly specific. The extract did not inactivate HIV extracellularly and did not inhibit the growth of herpes simplex, polio, or vesicular stomatitis viruses in human fibroblast culture. See R. S. Chang & H. W. Yeung, Antiviral Research, 9, 163–175 (1988).

Antiviral agents have been isolated from *Syzygium aromaticum, Sapium sebiferum, Scutellaria baicalensis,* and *Scutellaria rivularis*. Eugeniin (a tannin) isolated from *Syzygium aromaticum* and methyl gallate isolated from *Sapium sebiferum* exhibited anti-herpes simplex virus activity in vitro. Plant flavonoids, such as 5,7,4'-trihydroxy-8-methoxyflavone from the root of *Scutellaria baicalensis* and apigenin (5,7,4'-trihydroxyflavone) from the whole herb *Scutellaria rivularis,* were also reported to have anti-influenza virus activity. See (1) T. Hozumi, et al., U.S. Pat. No. 5,411,733 (1995); (2) M. Takechi & Y. Tanaka, Planta Medica, 42, 69–74 (1981); (3) C. J. M. Kane, et al, Bioscience Reports, 8, 85–94 (1988); and (4) T. Nagai, et al., Chem. Pharm. Bull., 38(5), 1329–1332 (1990).

Hozumi et al. disclose ninety one (91) herbal medicines which demonstrated antiviral activity. More specifically, fifty two (52) of them had antiherpesviral activity, sixty four (64) had antipolioviral activity, thirty seven (37) had anti-measles virus activity, twenty seven (27) had anti-varicella-zoster virus activity, twenty three (23) had anti-CMV activity, and twenty eight (28) had anti-DNA virus and anti-RNA virus activity. See T. Hozumi, T. Matsumoto, H. Ooyama, T. Namba, K. Shiraki, M. Hattori, M. Kurokawa, & S. Kadota, U.S. Pat. No. 5,411,733, issued on May 2, 1995.

The anti-DNA virus and anti-RNA virus activity of the twenty eight (28) herbal medicines disclosed in the '733 patent solely based upon their antiherpesviral, antipolioviral, anti-measles virus, and/or anti-varicella-zoster virus and anti-CMV activities. However, the extrapolation to cover both anti-DNA virus and anti-RNA virus activities is unfounded from the work conducted.

The data of the present invention presented below evidenced little or no anti-HIV activity of the two herbal medicines at 2.5 and 0.5 mg/mL derived from the rhizome of *Cyrtomium fortunei* and the bark of *Phellodendron amurense*. In contrast, the three (3) herbal medicines using the spike of *Prunella vulgaris*, the fruit of *Forsythia suspensa*, and the root and rhizome of *Polygonum cuspidatum*, will be shown to have a strong to moderate anti-HIV activity at 2.5 mg/mL.

Herbal medicines LONICERAE FLOS, BAPHICACANTHIS RHIZOMA ET RADIX, and FORSYTHIAE FRUCTUS have been used separately and/or in combination as antipyretic and detoxification agents along with other herbal medicines for treating acute hepatitis. The herbal medicines BLECHNI RHIZOMA and POLYGONI CUSPIDATI RHIZOMA have been used along with other herbal medicines in a formula for treating B hepatitis. The herbal medicines SCUTELLARIAE BARBATAE HERBA and LIGUSTRI FRUCTUS have occasionally been added to improve activity. Herbal medicine LIGUSTRI FRUCTUS was occasionally used along with other herbal medicines mainly as a tonic and HEDYOTIS was occasionally used along with other herbal medicines as a detoxification agent. The herbal medicine PRUNELLAE SPICA has also been used along with other herbal medicines to relief liver stress.

It is noted that in the practice of Chinese traditional medicine, herbal medicines were used to treat the symptoms of the patients, not the disease entity itself, and were therefore fairly nonspecific to a particular disease. Herbal medicines were used depending on the symptoms of the individual patient. The composition of herbal medicines would vary case by case and may even change for each individual patient during the course of the treatment according to each treatment result. It is therefore very difficult to have a universal herbal composition suitable for treating a specific disease within a population.

The present invention is directed to the discovery of antiviral herb compositions, extracts thereof and the active chemical constituents. The antiviral herb compositions of this invention are derived from individual herbs, herb mixtures and commercially available Chinese herbal medicines. These novel herb compositions and their extracts and/or active principles have demonstrated activities against viral diseases such as hepatitis B, hepatitis C, HBV and HCV carriers, HIV infection and AIDS.

SUMMARY OF THE INVENTION

As used herein and in the claims, the following nomenclatures will be used to identify the four (4) herb mixtures known as HHT888-4, HHT888-5, HHT888-45 and HHT888-54. HHT888-4 is a mixture of five single-herb Chinese herbal medicines at a preferred ratio of No.4(1): No.4(2): No.4(3): No.4(4): No.4(5) of about 3:3:3:3:4 (w/w). The weight ratio may vary up to 50% per component. By "variance of the weight ratio by 50%" means that each value of each component of the ratio may be increased or decreased by 50%. Thus, as an example, 1:1 can range from 1.5:0.5 to 0.5:1.5 (or 3:1 to 1:3).

HHT888-5 is a mixture of eleven (11) single-herb Chinese herbal medicines, No.5(1) to No.5(11) preferably at about equal proportions by weight. The weight ratio may vary up to 50% per component.

HHT888–45 is a mixture of four (4) to six (6) single-herb Chinese herbal medicines at a ratio of No.4(3): No.4(4): No.5(4): No.5(5): No.5(8): No.4(2) at a preferred ratio of about 1:1:1:1:0-1:0-1 (w/w). The weight ratio may vary up to 50% for each component.

HHT888-54 is a mixture No.5(5) and at least one single herb medicine selected from No. 4(2), No. 4(3), No. 4(4), No. 4(5), No. 5(1), No. 5(2), No. 5(4), No. 5(7), No. 5(8) and No. 5(11) wherein the weight ratio of No. 5(5) to each of the other single herb medicines is 1:1. Thus, HHT888-54 consists of No. 5(5) plus No. 4(3), No. 4(4) and No. 5(8); the most preferred weight ratio is 1:1:1:1.

More generally, the weight ratio of No. 5(5) to the sum of the other single herb medicines is from 1:10 to 10:1.

The single-herb components of HHT888-4 are:
No.4(1)=HEDYOTIS (a.k.a., OLDENLANDIAE HERBA) source: *Hedyotis diffusa* (a.k.a., *Oldenlandia diffusa*)
No.4(2)=SCUTELLARIAE BARBATAE HERBA source: *Scutellaria barbata, Scutellaria rivularis, Scutellaria dependens*
No.4(3)=LONICERAE FLOS source: *Lonicera japonica, Lonicera confusa*
No.4(4)=PRUNELLAE SPICA source: *Prunella vulgaris, Prunella vulgaris* subsp. *asiatica* (a.k.a., *Prunella vulgaris* var. *lilachina*)
No.4(5)=SOLANI HERBA source: *Solanum nigrum*

The single-herb components of HHT888-5 are:
No.5(1)=HEDYOTIS (a.k.a., OLDENLANDIAE HERBA) source: *Hedyotis diffusa* (a.k.a., *Oldenlandia diffusa*)
No.5(2)=BLECHNI RHIZOMA or DRYOPTERIS CRASSIRHIZOMAE RHIZOMA, source: *Blechnum orientale, Dryopteris crassirhizoma, Osmunda japonica, Woodwardia orientalis, Woodwardia unigemmata, Athyrium acrostichoides, Sphaeropteris lepifera, Cyrtomium falcatum, Cyrtomium fortunei*
No.5(3)=CIRSII RHIZOMA ET RADIX and BREEAE RADIX source: *Cirsium japonicum, Cirsium albescens, Cirsium japonicum* var. *australe, Breea segetum* (a.k.a., *Cephalanoplos segetum*), *Breea setosum*
No.5(4)=LESPEDEZAE HERBA or SENECINIS HERBA source: *Lespedeza cuneata, Senecio scandens*
No.5(5)=AEGINETIAE HERBA(a.k.a. GOLDEN LOCK KEY or LOTUS HERBA). source: *Aeginetia indica, Dichondra micrantha, Striga lutea, Dichondra repens*
No.5(6)=BAPHICACANTHIS RHIZOMA ET RADIX source: *Baphicacanthes cusia, Strobilanthes cusia, Isatis tinctoria, Isatis indigotica, Polygonum tinctorium*
No.5(7)=POLYGONI CUSPIDATI RHIZOMA source: *Polygonum cuspidatum, Polygonum runcinatum, Polygonum reynoutria* (a.k.a., *Reynoutria japonica*)
No.5(8)=FORSYTHIAE FRUCTUS source: *Forsythia suspensa, Forsythia viridissima, Forsythia koreana*
No.5(9)=PHELLODENDRI CORTEX source: *Phellodendron amurense, Phellodendron chinense, Phellodendron amurense* var. *sachalinense, Phellodendron wilsonii*
No. 5(10)=BLETILLAE TUBER source: *Bletilla striata*
No.5(11)=FLIGUSTRI FRUCTUS source: *Ligustrum lucidum, Ligustrum japonicum*

The single-herb components of HHT888-45 are:
No.4(3)=LONICERAE FLOS source: *Lonicera japonica, Lonicera confusa*
No.4(4)=PRUNELLAE SPICA source: *Prunella vulgaris, Prunella vulgaris* subsp. *asiatica* (a.k.a., *Prunella vulgaris* var. *lilachina*)
No.5(4)=LESPEDEZAE HERBA or SENECINIS HERBA source: *Lespedeza cuneata, Senecio scandens*
No.5(5)=AEGINETIAE HERBA (a.k.a. GOLDEN LOCK KEY or LOTUS HERBA). source: *Aeginetia indica* in addition to No.5(5) are at least one selected from:
No.4(2)=SCUTELLARIAE BARBATAS HERBA (optional) source: *Scutellaria barbata, Scutellaria rivularis, Scutelaria dependens*
No.5(8)=FORSYTHIAE FRUCTUS (occasionally used) source: *Forsythia suspensa, Forsythia viridissima, Forsythia koreana*

The single herb components of HHT888-54 in addition to No.5(5) are at least one selected from:

No.4(2)=SCUTELLARIAE BARBATAE HERBA source: *Scutellaria barbata, Scutellaria rivularis, Scutellaria dependens*

No.4(3)=LONICERAE FLOS source: *Lonicera japonica, Lonicera confusa*

No.4(4)=PRUNELLAE SPICA source: *Prunella vulgaris, Prunella vulgaris* subsp. *asiatica* (a.k.a., *Prunella vulgaris* var. *lilachina*)

No.4(5)=SOLANI HERBA source: *Solanum nigrum*

No.5(1)=HEDYOTIS (a.k.a., OLDENLANDIAE HERBA) source: *Hedyotis diffusa* (a.k.a., *Oldenlandia diffusa*)

No.5(2)=BLECHNI RHIZOMA or DRYOPTERIS CRASSIRHIZOMAE RHIZOMA, source: *Blechnum orientale, Dryopteris crassirhizoma, Osmunda japonica, Woodwardia orientalis, Woodwardia unigemmata, Athyrium acrostichoides, Sphaeropteris lepifera, Cyrtomium falcatum, Cyrtomiumfortunei*

No.5(4)=LESPEDEZAE HERBA or SENECINIS HERBA source: *Lespedeza cuneata, Senecio scandens*

No.5(7)=POLYGONI CUSPIDATI RHIZOMA source: *Polygonum cuspidatum, Polygonum runcinatum, Polygonum reynoutria* (a.k.a., *Reynoutria japonica*)

No.5(8)=FORSYTHIAE FRUCTUS source: *Forsythia suspensa, Forsythia viridissima, Forsythia koreana*

No.5(11)=LIGUSTRI FRUCTUS source: *Ligustrum lucidum, Ligustrum japonicum*

The names of the Chinese herbal medicines for the single-herb components are shown in capital letters, followed by their plant sources listed in italics.

As used herein and in the claims, the term HHT888-4, HHT888-5, HHT888-45 and the like include the actual herbal blends, aqueous extracts thereof and the individual active components or principles of the extract. In similar fashion, the use of the terms No.5(5), No. 5(8) and the like include the actual herb, extracts thereof and the isolated active molecular agents.

As also used in the specification and in the claims, No.4(2), No.4(3), No.4(4), No.4(5), No.5(1), No.5(2), No.5 (3), No.5(4), No.5(5), No.5(6), No.5(7), No.5(8), No.5(9), No.5(10), and No.5(11) are the single-herb components described above, including their respective source plants. It should be noted that No.4(1) is the same as No.5(1) (HEDYOTIS).

Specific details and descriptions of the above recited Chinese herbal medicines and medicinal herbs can be found in the following references: (1) H. C. Chang, Medicinal Herbs I, Holiday Publishing Co., Taipei, Taiwan, R.O.C., 15, 36, 100, 113, 127, 147 (1990); (2) H. C. Chang, Medicinal Herbs II, Holiday Publishing Co., Taipei, Taiwan, R.O.C., 15, 131, 135, 155 (1991); (3) W. S. Kan, Pharmaceutical Botany, National Research Institute Of Chinese Medicine, Taipei, Taiwan, R.O.C., 113, 124–130, 200–201, 206–207, 289–290, 353–354, 442–444, 485, 487–488, 497, 505, 513–514, 522, 527–529, 558, 562–563, 648–649 (1971); (4) M. S. Lee, Frequently Used Chinese Crude Drugs And Folk Medicines Handbook, 12th Ed., Sheng-Chang Medicinal Record Magazine Publishing Co., Taipei, Taiwan, R.O.C., 4–6, 17, 21, 29, 36, 38, 40, 48, 64, 71, 79, 85 (1992); and (5) H. Y. Hsu, Y. P. Chen, S. G. Hsu, J. S. Hsu, C. J. Chen, & H. C. Chang, Concise Pharmacognosy, New Medicine Publishing Co., Taipei, Taiwan, R.O.C., 90, 97, 105–106, 117–118, 126–127, 130–131, 133, 144–145, 152–153, 156–157, 161–162, 174, 176–177, 357–358, 381–382, 384–385, 456–457, 577–578 (1985).

The present invention in its broadest aspect relates to the use of the described herbal medicines and various mixtures thereof to prevent and treat viral infections. More specifically, the viral infections are those caused by HBV, HCV and HIV. The antiviral mixtures according to the invention have been described above as HHT888-4, HHT888-5, HHT888-45 and HHT888-54. In addition, the single herb agents designated No. 4(2), No. 4(5), No. 5(5), No. 5(7), No. 5(8) and No. 5(11) have been shown to have antiviral activity. These single herb agents have not been shown by the prior art to have antiviral activity.

A more specific aspect of the present invention resides in the discovery that HHT888-5 is efficacious in reducing hepatitis B viruses in HBV carriers. An additional aspect of the invention resides in the discovery that HHT888-45 is efficacious in treating hepatitis C patients and returning their liver function to normal.

The herb mixtures HHT888-4 and HHT888-5 and their aqueous extracts have both been shown by the inventors herein to also have antiretroviral activities against MuLV and HIV in vitro. In addition, eleven (11) of the fifteen (15) single-herb components of HHT888-4 and HHT888-5, i.e., No.4(2), No.4(3), No.4(4), No.4(5), No.5(1), No.5(2), No.5 (4), No.5(5), No.5(7), No.5(8), and No.5(11) have shown anti-HIV activities by effectively suppressing viral proliferation in HIV infected human peripheral blood lymphocytes (PBLs).

There is further disclosed as a composition of matters, the herb mixtures HHT888-4, HHT888-5, HHT888-45 and HHT888-54. As described above, HHT888-54 is No.5(5) or its extract or active principle and at least one single-herb herbal medicine or its extract or active principle selected from the group consisting of No.4(2), No.4(3), No.4(4), No.4(5), No.5(1), No.5(2), No.5(4), No.5(7), No.5(8), and No.5(11). These compositions of matter have not been described before and are unobvious.

There is further disclosed a method of treating viral infections in a mammal, said method comprising administering to said mammal from 0.4 to 120 g per day of at least one composition selected from the group consisting of HHT888-4, HHT888-5, HHT888-45, HHT888-54, No. 4(2), No. 4(5), No. 5(1), No. 5(2), No. 5(4), No. 5(5), No. 5(7), No. 5(8), No. 5(11) and their respective extracts or active principles.

More specifically, there is disclosed a method for reducing the viral load of humans infected with hepatitis B virus, said method comprising administering to said human a therapeutically effective amount of a composition comprising HHT888-5.

There is also disclosed a method for reducing the viral load of humans infected with hepatitis C virus, said method comprising administering to said human a therapeutically effective amount of a composition comprising HHT888-45.

There is also disclosed a method of reducing the viral load of a human carrier of the hepatitis B virus and a method of preventing hepatitis B in a human, said method comprising administering to said human a therapeutically effective amount of a composition comprising No.5(5) and at least one selected from the group consisting of No.5(1), No.5(2), No.5(3), No.5(4), No.5(6), No.5(7), No.5(8), No.5(9), No.5 (10), and No.5(11). There is further disclosed a method of treating a hepatitis C virus carrier and a method of treating or preventing hepatitis C in a human, said method comprising administering to said human a therapeutically effective amount of a composition comprising the mixture of the single-herb herbal medicine No.5(5), its extract or active principle and at least one single-herb herbal medicine, its extract or active principle selected from the group consisting of No.4(2), No.4(3), No.4(4), No.5(4), No.5(8), and No.5 (11).

Also disclosed is a method of treating hepatitis B in a human, said method comprising administering to said human a therapeutically effective amount of at least one composition selected from HHT888-45 and HHT888-5.

There is disclosed a method of treating hepatitis B in a human, said method comprising administering to said human a therapeutically effective amount of at least one composition selected from: 1) a mixture of the single herb medicine No. 5(5), its extract or active principle and at least one single-herb herbal medicine, its extract or active principle selected from the group consisting of No.4(2), No.4(3), No.4(4), No.5(4), No.5(8), and No.5(11); and 2) a mixture of the single-herb herbal medicine No.5(5), its extract or active principle and at least one single-herb herbal medicine, its extract or active principle selected from the group consisting of No.5(1), No.5(2), No.5(3), No.5(4), No.5(6), No.5(7), No.5(8), No.5(9), No.5(10), and No.5(11).

There is further disclosed a method for treating humans infected with HIV, said method comprising administering to said human a therapeutically effective amount of a composition comprising HHT888-4.

There is disclosed a method for treating humans infected with HIV, said method comprising administering to said human a therapeutically effective amount of a composition comprising HHT888-5.

There is disclosed a method for treating humans infected with HIV, said method comprising administering to said human a therapeutically effective amount of a composition comprising HHT888-45.

There is disclosed a method for treating humans infected with HIV, HBV and HCV said method comprising administering to said human a therapeutically effective amount of a composition comprising HHT888-54.

There is also disclosed a method for treating humans infected with HIV, said method comprising administering to said human a therapeutically effective amount of a composition comprising at least one single-herb herbal medicine, its extract or active principle selected from the group consisting of No.4(2), No.4(5), No.5(1), No.5(2), No.5(4), No.5 (5), No.5(7), No.5(8), and No.5(11).

There is also disclosed a method of treating humans infected with HIV, said method comprising administering to said human a therapeutically effective amount of a composition comprising the mixture of the single-herb herbal medicine No.5(5), its extract or active principle and at least one single-herb herbal medicine, its extract or active principle selected from the group consisting of No.4(2), No.4(3), No.4(4), No.4(5), No.5(l), No.5(2), No.5(4), No.5(7), No.5 (8), and No.5(11).

The dosage of the compositions of the invention can range from 0.4 to 120 g per day for the mammal in need of therapy. One skilled in the art will appreciate that depending upon the weight of the individual and the progression of the viral infection, that higher doses of the compositions will be required. As the compositions according to the invention have demonstrated virtually no side effects, high doses may be initiated with reduction of dosage upon manifestation (i.e., reduction of viral load) of therapeutic effect. One skilled in the art can tailor each dosage rate for a given individual without undue experimentation. More specifically, the dosages for a given composition can range from 0.4 to 25 g per day. Preferably, the compositions are administered at least three (3) times per day however, bolus administration will be effective. More specifically, oral dosages of 5.5 g three (3) times a day (total 16.5 g per day) of the herb mixture HHT888-5 have been found to be effective to reduce HBV load in carriers. Oral dosages of 2.7–5.7 g three times a day (total 8–17 g per day) of the herb mixture HHT888-45 have been found to be effective to return normal liver function to hepatitis C patients. Dosages as high as 121 g per day for HHT888-5 and 63 g per day for HHT888-45 have not evidenced serious side effects. It will be appreciated that the dosages recited herein are for the herbal medicine (extract deposited on ground plant) in dry form. Further, extracts of the inventive compositions will increase the concentration of the actives and therefore reductions in the dosage levels will be realized. Dosages as low as 10% of those recited herein for the inventive compositions are contemplated.

The preferred dosage for No. 5(5) to treat HCV infection is from 0.4 to 17 g per day.

The compositions of the invention are preferably administered enterally, however, intravenous (i.v.) and/or intramuscular (i.m.) administration is also contemplated herein. Those skilled in the art will understand how i.v. and i.m. formulations can be prepared and how the effective dosages can be obtained.

In the method according to this invention a mammal may be a human or animal. The human may be an adult, child or infant. Thus, for infants, an infant formula containing the hereinafter described plant extracts or active principles will be effective in treating the infants infected with HBV, HCV, or HIV. For children and adults, a medical food or nutritional product, such as milks and yogurts, containing the plant extracts or active principles described herein will also be effective in treating humans infected with HBV, HCV, or HIV.

The herbs used as starting materials for this invention may be obtained from commercial sources as single-herb herbal medicines which may be mixed, or extracted and concentrated, and placed in compositions for the administration to a human. The plant extracts, once isolated from the plant material, may be concentrated and then placed in compositions for the administration to a human. The active principles, once isolated from the plant material or herbal medicine, may be concentrated and then placed in compositions for the administration to a human. The compositions of this invention may take a variety of forms such as capsules, tablets, powder, candies, gels, beverages, teas, nutritional products, and the like.

Also disclosed is a medicinal product produced by the process comprising the steps of: (a) contacting comminuted plant material selected from the group consisting of No.5(1) to No.5(11), No.4(2) to No.4(5), and mixtures thereof, with water to form an aqueous dispersion; (b) heating the aqueous dispersion to about 100° C. and holding at that temperature for about 0.5 to about 3 hours; (c) separating the insoluble plant material from the aqueous phase; and (d) concentrating the solute contained in the aqueous phase. The concentrated solute may be obtained through freeze drying, spray drying, evaporation and ultrafiltration.

As described in more detail in the following examples, the herbal compositions of the invention contain components that are active against viruses in vitro and in vivo.

Most impressively, the clinical effects of HHT888-5 on hepatitis B virus carriers are shown in Table 1 while the clinical effects of HHT888-45 on type C hepatitis patients are shown in Table 6.

In a preferred embodiment, the herb mixtures, individual single-herb herbal medicines, their water extracts and/or active principles are incorporated into oral dosage forms such as capsules, tablets, teas, powders, candies, candy bars, beverages, nutritional products, and the like.

This application sets forth the data available on the present discoveries and fully describes the compositions of matter, their preparation, and clinical applications. These and other aspects of the invention will become apparent to those skilled in the art as a result of the following examples which are intended as illustrative of the invention and not limitative.

BEST MODE FOR CARRYING OUT THE INVENTION

To acquaint persons skilled in the art with the principles of the invention, the following Examples are submitted.

EXAMPLE 1
Preparation of Herb Mixtures

In the preparation of the herbal compositions according to the invention, Chinese herbal medicines in single herb format were obtained from commercial sources in powder form. The individual single-herb herbal medicines were mixed in the appropriate proportions to prepare each herb mixture.

The herb mixture HHT888-4 was prepared by mixing five (5) single-herb herbal medicines No.4(1), No.4(2), No.4(3), No.4(4), and No.4(5) at a ratio of 3:3:3:3:4 by weight. The herb mixture HHT888-5 was prepared by mixing equal weights of eleven (11) single-herb herbal medicines No.5 (1), No.5(2), No.5(3), No.5(4), No.5(5), No.5(6), No.5(7), No.5(8), No.5(9), No.5(10), and No.5(11).

The herb mixture HHT888-45 was prepared by mixing four (4) to six (6) single-herb herbal medicines No.4(3), No.4(4), No.5(4), No.5(5), No.5(8), and No.4(2) at a ratio of 1:1:1:1:0-1:0-1 by weight. The single-herb herbal medicine No.5(8) or No.4(2), or both, were not used in some cases in HHT888-45 for initial administrations. One of the two single-herb herbal medicines or both were added later when needed to enhance the therapy. The weight ratio of the single-herb herbal medicine No.4(2) in the herb mixture HHT888-45 also varied case-by-case between 0.5 and 1 when used.

It is noted that a mixture of decoctions prepared individually from the source plants of the single-herb herbal medicines or a decoction prepared from the pre-mixed source plants of the single-herb components of each herb mixture is well within the specification of the herb mixture.

EXAMPLE 2
Preparation of Single-herb Herbal Medicines

The single-herb herbal medicine used to prepare the herb mixtures has been described in the Prior Art section of this application. The plant source from which each single-herb herbal medicine is obtained was also listed in the Prior Art section. More than one species or genus of medicinal plant may be used to prepare the same herbal medicine as indicated in the plant source list of that herbal medicine. For example, the herbal medicine No.5(8) or FORSYTHIAE FRUCTUS may be prepared from either one of the three (3) species of Forsythia genus plants, i.e., *Forsythia suspensa, Forsythia viridissima, Forsythia koreana* or mixtures thereof. The herbal medicine No.5(6) or BAPHICA-CANTHIS RHIZOMA ET RADIX may be prepared from one of the five (5) plants of different genus and species, i.e., *Baphicacanthes cusia, Strobilanthes cusia, Isatis tinctoria, Isatis indigotica, Polygonum tinctorium* or mixtures thereof The herbal medicines were prepared from their respective plant sources as follows.

A suitable part or parts or the whole herb of a medicinal plant was obtained, washed with cold water, dried and comminuted. The plant materials were then extracted with boiling water on a basis of 1 part by weight of plant material to approximately 5 to 10 parts by weight of water. The amount of water used should at least cover the plant material in the extraction vessel. Samples were boiled for 0.5 to one hour, but not in excess of 3 hours, in order to allow effective extraction of the desired components. Shorter or longer heating would not substantially affect the extraction, except the yield and cost. The aqueous solution was separated from the plant material by filtration.

The aqueous solution may be freeze dried or spray dried, or reduced in volume by heating with or without an applied vacuum. The concentrate may then be spray dried or freeze dried or absorbed by powdered material of the same plant material or starch and thus the single-herb herbal medicine is prepared in powdered form.

It is noted that a decoction prepared from a source plant of the single-herb herbal medicine is well within the specification. A decoction is the aqueous solution of the plant material prepared by boiling the plant material in water as described above for about 0.5 to one hour. The decoction may be directly consumed after it is prepared and cooled to warm or ambient temperatures or preserved with proper sterilization for later consumption. Sterilization may be accomplished by microfiltration or heat.

EXAMPLE 3
Treatment of Hepatitis B Virus Carriers

Twenty-nine (29) HBV carriers with normal levels of serum liver enzymes, glutamine oxalacetate transferase (SGOT) and glutamine pyruvate transferase (SGPT), were treated with HHT888-5. Several HBV carriers who had elevated SGOT and SGPT levels were first treated with other remedies which returned their serum liver enzymes to normal levels (8–40 unit/mL for SGOT and 5–35 unit/mL for SGPT) but failed to reduce the HBV load. Treatment with HHT888-5 then began. HHT888-5 was prepared as described in Example 1 by mixing eleven (11) single-herb herbal medicines which were obtained from a commercial source and were manufactured following good manufacture practice (GMP) guidelines. Consent of the patients was obtained before their treatment began.

Patients were instructed to take the HHT888-5 three (3) times a day. Each dose was 5.5 g. Each 5.5 g packet of the herb mixture was mixed with warm water and consumed orally. Serum hepatitis B surface antigen (HBsAg) titers of each patient were determined at intervals as shown in Table 1 to monitor the progress of the treatment. Serum HBsAg titer was determined using a reverse-passive hemagglutination test as described herein: (1) Instruction of "Taifu" Serodia-HBs Test Reagent for HBsAg Detection, Taifu Pharmaceutical Co., Ltd., Taoyuan, Taiwan, R.O.C.; (2) D. S. Chen & J. L. Sung, J. Formosan Med. Assoc., 77, 263–270 (1978); and (3) T. Juji & T. Yokochi, Japan. J. Exp. Med., 39, 615–620 (1969).

Table 1 shows the treatment results of the twenty-nine (29) HBV carriers. Individual patients showed progressive improvement in their disease state over the course of treatment, as indicated by their HBsAg titer reductions and well being. Fourteen (14) carriers (48%) whose HBsAg titers ranged from 20 to 81,920 were significantly lowered (four (4) to 256-fold reductions, or from positive to negative) after 35 to 964 days of treatment. Four (4) carriers (14%) reduced their HBsAg titers from 20, 40, and 2,560 to negative (i.e., below 20 ng/mL detection level) after 56–153 days of treatment. Fourteen (14) carriers (48%) had no significant change (two-fold titer decrease or increase or no change) in HBsAg titers. That means these carriers had static HBsAg titers during the course of the treatment (63–284 days). One carrier (3%) had a slightly four-fold titer increase.

The above HHT888-5 treatment results compare very favorably with the current interferon therapy. The response rates for interferon therapy and HHT888-5 treatment to lower the HBsAg titers in patients infected with HBV were comparable, approximately 40% vs. 48%. The serum HBsAg clearance rates were also comparable for both, 10–15% for interferon therapy and approximately 14% for HHT888-5 treatment. Furthermore, the interferon therapy is administered intramuscularly or intravenously and with frequent adverse effects. The HHT888-5 treatment is administered orally (like drinking a tea) and no apparent side effects were observed in all patients treated. Oral administration is a much more convenient and better way than intramuscular or intravenous administration. HHT888-5 can thus be safely and conveniently consumed even on a long-term basis to reduce or control HBV proliferation in HBV carriers and hepatitis B patients.

TABLE 1

Clinical Effects of HHT888-5 on Hepatitis B Virus Carriers

| Patient | HBsAg Titer Before | HBsAg Titer After | Duration (days) |
|---|---|---|---|
| 1 | 40 | negative | 56 |
| 2 | 2560 | negative | 72 |
| 3 | 20 | negative | 153 |
| 4 | 20 | negative | 88 |
| 5 | 2560 | 80 | 53 |
| 6 | 1280 | 320 | 101 |
| 7 | 2560 | 1280 | 32 |
|   |      | 1280 | 399 |
|   |      | 320  | 964 |
| 8 | 2560 | 1280 | 79 |
|   |      | 640  | 412 |
| 9 | 20480 | 5120 | 53 |
| 10 | 20480 | 5120 | 60 |
| 11 | 40960 | 10240 | 35 |
| 12 | 81920 | 40960 | 74 |
|   |       | 10240 | 461 |
| 13 | 81920 | 20480 | 63 |
| 14 | 5120 | 2560 | 170 |
|   |      | 2560 | 245 |
|   |      | 1280 | 556 |
|   |      | 1280 | 832 |
| 15 | 160 | 80 | 284 |
| 16 | 320 | 160 | 198 |
| 17 | 640 | 320 | 276 |
| 18 | 1280 | 640 | 120 |
| 19 | 2560 | 1280 | 69 |
| 20 | 5120 | 2560 | 263 |
| 21 | 20480 | 10240 | 77 |
| 22 | 40960 | 40960 | 120 |
|   |       | 20480 | 210 |
| 23 | 160 | 160 | 227 |
| 24 | 320 | 320 | 79 |
| 25 | 640 | 640 | 157 |
| 26 | 1280 | 1280 | 69 |
| 27 | 40960 | 40960 | 137 |
| 28 | 5120 | 10240 | 63 |
| 29 | 160 | 640 | 121 |

When the HBV viral load in an HBV carrier can be reduced or maintained at a sufficiently low level, the carrier is less likely to progress to hepatitis, liver cirrhosis, liver cancer, and death. Thus, HHT888-5 may be used to prevent and treat hepatitis B, or even prevent liver cirrhosis or liver cancer caused by HBV infection.

Since HHT888-5 was administered in the above treatments by mixing the powder in water first and then consumed orally, the water extract of HHT888-5 or a decoction from the herbal mixture comprising the single-herb components or plants of HHT888-5 is expected to be also effective and safe. Isolation of the active components of HHT888-5 and its administration to humans would also be efficacious in the treatment of HBV.

It is noted that HHT888-5 may be administered "as is" or in other solid dosage forms such as capsules, tablets, tea bags, candies, etc. The powdered herb mixture is typically mixed with warm or cold water and consumed orally. Its extracts may be administered as capsules, tablets, teas, candies, beverages, nutritional products, and the like.

Dosages range from 1 to 5 treatments per day at about 1 to 120 g per dosage depending upon the form and concentration of the herbal medicine. The effective minimum dose of a composition as a dried water extract of HHT888-5 is 1 g per day. The effective minimum dose of a composition comprising a more purified active component or components would be lower. The water extract of the tested HHT888-5 constituted 19% of the herb mixture by weight. Dosages of the herb mixture HHT888-5 as high as 120 g per day have been accomplished without serious side effects.

EXAMPLE 4

Antiretroviral Testing of Herb Mixtures and their Water Extracts

Two herb mixtures, HHT888-4 and HHT888-5, were tested for their antiretroviral activities and found to be active against EMuLV and HIV in the in vitro assay. Two in-vitro assays, anti-Ecotropic Murine Leukemia Virus (anti-EMuLV) and anti-HIV, were used to test the antiretroviral activities of the inventive compositions.

The anti-EMuLV assay uses a large, enveloped, RNA-containing retrovirus, EMuLV, which belongs to the same virus family as HIV and has many characteristics that are similar to HIV.

1. Anti-Ecotropic Murine Leukemia Virus Assay

The assay contained two parts, cytotoxicity test and virus suppression test. See QBI Protocol 39014 Final Report and QBI Protocol 39016 Final Report, Quality Biotech, Camden, N.J., USA, 1992. Each sample was initially tested for its cytotoxicity to the SC-1 indicator cells which were used for titration of infectious EMuLV in a XC plague assay. See QBI protocol C30015, Quality Biotech, Camden, N.J., USA. Each sample was dispersed in a virus resuspension buffer (50 mM Tris, pH 7.8, 10 mM KCL, 0.1 mM EDTA) without the virus. The solution was then subjected to the XC plague assay under the same conditions as those for the determination of EMuLV titer. A sample was considered cytotoxic if the indicator cells for the assay were less than 50% confluent. A noncytotoxic sample concentration was chosen for the virus suppression test.

In the virus suppression test, each sample was incubated with EMuLV (strain AKV623, titer $2.2$–$4.2\times10^5$ PFU/mL) in a virus resuspension buffer at 23–25 mg/mL (e.g., 100 mg/4.0 mL) for 12–32 minutes. The treated virus suspension was pH adjusted, if necessary, to within 6.8–7.2 and then tested for its titer in the XC plague assay.

An aliquot (1.5 mL) was diluted in the cell culture medium to the endpoint ($10^0$, $10^{-1}$, $10^{-2}$, $10^{-3}$, $10^{-4}$, $10^{-5}$, $10^{-6}$, $10^{-7}$, and $10^{-8}$ dilutions, or as appropriate). Each dilution was vortexed to resuspend any particulates if present and assayed in duplicate for infectious viral particles by the XC plaque assay. A positive control (virus suspension without treatment) and a negative control (cell culture medium, no virus) were also analyzed concurrently to validate the assay.

Anti-EMuLV activity of the sample was expressed in $\log_{10}$ reduction of the EMuLV titer when compared to the positive control. A sample with $\log_{10}$ to titer reduction greater than 0.5 is considered to be active.

HHT888-4 and HHT888-5 were initially tested "as is" and exhibited good antiviral activities (1.0 to 1.4 $\log_{10}$ reduction in viral titer) at 25 mg/mL and 12 minutes of incubation with the virus at room temperature. They were then tested again with a longer incubation time (32 minutes) with the virus at the same concentration. Each sample was also tested for its soluble and insoluble fractions in the above virus resuspension buffer to see if any active component was water soluble. The soluble portion was separated from the insoluble one by centrifuge at room temperature and 10,000x g for 10 minutes. The soluble fraction was divided into two aliquots, one 0.45-$\mu$m filtered and one unfiltered, and tested to see if residual particulates have any effect on the activity.

Table 2 summarizes the anti-EMuLV activity test results. The results confirmed that both HHT888-4 and HHT888-5 and their soluble and insoluble fractions have anti-EMuLV activities. The samples caused 1.0 to 2.6 $\log_{10}$ reduction in viral titer when they were incubated with the virus at 23–25 mg/mL for 32 minutes. Microfiltration did not significantly affect the activity of either soluble fraction.

2. Anti-Human Immunodeficiency Virus Assay

This assay also contained two parts, a toxicity test and a HIV suppression test. The sample was mixed in a cell culture medium, e.g., 50 mg in 1.00 mL. The mixture was vortexed and centrifuged to separate the soluble from the insoluble. The supernate was filtered through a 0.45-$\mu$m filter and then diluted with cell culture medium to appropriate concentrations for the assay. The cell culture medium used in the assay was RPMI 1640 (pH 7.3±0.3) supplemented with 10% fetal calf serum, 2 mM glutamin, 50 U/mL penicillin and 50 $\mu$g/mL streptomycin.

The sample was tested for its cytotoxicity and/or cytostatic activity towards the target cells, human peripheral blood lymphocytes (PBLs). A lymphocyte proliferation assay was used for the toxicity test, where a 100 $\mu$L sample was incubated with 100 $\mu$L of a cell suspension of uninfected PBLs (3×10$^5$ cells) under the same conditions as the HIV suppression test. Lymphocyte proliferation was measured by a colorimetric assay (MTT-Test). See T. Mosmann, J. Immunological Methods, 65, 55–63 (1983). A sample concentration which results in $\geq$70% of the control in lymphocyte proliferation is considered to be acceptable for the HIV suppression test.

In the HIV suppression test, HIV-1 infected PBLs were cultivated in the presence of the sample for four (4) days as in the toxicity test. See H. Ruebsamen-Waigmann, et al., J. Med. Virology, 19, 335–344 (1986). The secreted viral core protein p24 and/or viral RNA were determined as indicators for virus proliferation status on day 3 and day 4 by an HIV-1 p24 capture ELISA technique and an HIV-RNA dot blot hybridization technique, respectively. The concentration of p24 synthesized by the HIV infected cells was determined by Sandwich ELISA. A standard preparation of recombinant p24 (MicroGeneSys, USA) was used for calibration of the ELISA. See Ch. Mueller, et al., Fresenius Z. Anal. Chem., 330, 352–353 (1988).

HIV-RNA synthesized in the infected cells was determined by a nucleic acid hybridization technique. Cellular RNA was prepared from the infected cells and analyzed by a dot blot hybridization technique. The hybridization solution contained the P$^{32}$-labeled DNA probe which comprised a 5.5 kilobase DNA fragment of the HIV isolate D$_{31}$. See H. v. Briesen, et al., J. Med. Virology, 23, 51–66 (1987). This fragment covering the gag/pol region of the virus is labeled with P$^{32}$ alpha-d CTP by oligonucleotide labeling. Plus-strand RNA transcripts derived from the gag/pol region of the viral isolate D$_{31}$ were used as the external standard for the hybridization. These "run-off" transcripts were generated by means of the T7 polymerase reaction from negatively polarized HIV-DNA under T7-promotor control. The concentration of RNA transcripts was determined spectrophotometrically. The hybridized probe was detected by autoradiography and the processed autoradiograms were evaluated densitometrically.

A positive control, a negative control, and an AZT control were conducted concurrently to assure the validity of the

TABLE 2

Anti-Ecotropic Murine Leukemia Virus Activity

| Sample | Treatment | Cytotoxicity* | | | Anti-EMuLV Activity |
| | | 25 | 2.5 | 0.25 mg/mL | $\log_{10}$ Titer Reduction** |
| --- | --- | --- | --- | --- | --- |
| HHT888-4 | "as is" | Yes | No | No | 1.02 (90%)*** |
| | "as is" | Yes | No | No | 1.04 (91%)**** |
| | Soluble | — | — | — | 1.74 (98%)**** |
| | Soluble, filtered | — | — | — | 1.59 (97%)**** |
| | Insoluble | — | — | — | 2.64 (99.8%)**** |
| HHT888-5 | "as is" | Yes | No | No | 1.35 (96%)*** |
| | "as is" | Yes | No | No | 2.10 (99.2%)**** |
| | Soluble | — | — | — | 2.05 (99.1%)**** |
| | Soluble, filtered | — | — | — | 1.71 (98.1%)**** |
| | Insoluble | — | — | — | 1.72 (98.1%)**** |

*Sample was considered cytotoxic if the SC-1 indicator cells for the assay were less than 50% confluent.
**As compared to a working virus suspension with a titer of 2.2–4.2 × 10$^5$ PFU/mL, or $\log_{10}$ (PFU/mL) = 5.34–5.62. The values in parentheses indicate percent reductions in viral titer from the working virus suspension.
***Incubation time 12 minutes, at 25 mg/mL test level. The activity may be caused by the sample, by microbial contaminant, or by a non-specific physical interaction between the particles of the sample and the virus, since the samples were not sterile filtered before assay.
****Incubation time 32 minutes, at 25 mg/mL test level for the "as is" unfractionated samples. For soluble, soluble & sterile filtered, and insoluble fractions, the test level was equivalent to 23 mg/mL of its unfractionated sample.

HIV suppression test. All tests were performed in triplicates, and 96-well round bottom microtiter plates were used for all assays. A positive control was HIV-1 infected lymphocytes cultivated in the presence of the cell culture medium without the sample. A negative control was lymphocytes infected with a heat-inactivated virus inoculum incapable of replication. These "mockinfected" lymphocytes were cultivated and assayed in the same way as the infected cells. The amount of viral protein being present in the cultures solely due to the remaining inoculum was thus determined as the background level. The amount of viral protein p24 in the test sample and in the positive control due to viral replication was then determined by the respective p24 levels less the background level.

The amount of viral protein being present in the cultures containing the sample due to viral proliferation was compared with that in the positive control, i.e., the culture without the sample. The % suppression of HIV proliferation was determined by the difference in p24 levels between the positive control and the sample, divided by the p24 level of the positive control, and timed 100%.

The AZT control was conducted via HIV-1 infected lymphocytes that were cultivated in the presence of azidothymidine (AZT) at concentrations of 100, 10, 1 and 0.1 ng/mL, respectively. This provided an estimate of the sensitivity of the lymphocytes towards AZT, a known inhibitor of HIV-1 replication. The suppression of HIV-1 proliferation caused by AZT in a concentration of 10 ng/mL should be greater than 50% as compared to the untreated positive control.

on viral protein p24 and 99–100% suppression based on viral RNA determined on both day 3 and day 4 after treatment. The anti-HIV activity at 50 µg/mL was negligible, 0–12% suppression for both herb mixtures. The activities could not be attributed to insoluble particulates since they were filtered out by a 0.45-µm filter before the assay. The activities were not due to cytotoxicity. Repeat tests on three lots of HHT888-4 showed 100% suppression at 2.5 mg/mL on both day 3 and day 4 with acceptable cytotoxicity (71–100% of control proliferation). Repeat tests on three lots of HHT888-5 at 2.5 mg/mL showed 93–98% suppression on day 3 and 89–99% suppression on day 4 with acceptable cytotoxicity (85–91% of control proliferation). Results of the repeat experiments are shown in Table 4.

It is noted that Lot 3 of HHT888-4 or HHT888-5 was prepared by mixing the respective single-herb components at equal proportion by weight. Lot 3 of HHT888-5 was composed of nine (9) single-herb components, excluding No.5(10) and No.5(11).

Water extracts of HHT888-4 and HHT888-5 from one to two lots were further tested to see whether the active components were extractable by water. Water extracts of HHT888-4 and 5 were prepared by extracting 5 g of the powder with 25 mL of MilliQ purified water twice. Each water suspension was vortexed for 1 minute, stood for 5 minutes, and vortexed again for 1 minute to facilitate the extraction. The extract was separated from the insoluble by centrifuge at 1,000–2,000 rpm for 20 minutes. The supernate

TABLE 3

Anti-HIV Activities of HHT888-4 and HHT888-5

| Sample | Test Concentration | Cytotoxicity* | HIV Suppression p24 Day 3 | p24 Day 4 | RNA Day 3 | RNA Day 4 |
|---|---|---|---|---|---|---|
| HHT888-4 | 2.5 mg/mL | >46% | 100% | 100% | 100% | 100% |
|  | 50 µg/mL | 85% | 1% | 6% | — | — |
| HHT888-5 | 5.0 mg/mL | 75% | 100% | 97% | 99% | 100% |
|  | 50 µg/mL | 86% | 0% | 12% | — | — |
| AZT | 100 ng/mL | — | 99–100% | 100% | — | — |
|  | 10 ng/mL | — | 85–98% | 77–96% | — | — |
|  | 1 ng/mL | — | 20–39% | 8–12% | — | — |
|  | 0.1 ng/mL | — | 0% | 0–3% | — | — |

*Percent proliferation of control. HHT888-4 was 46% at 5.0 mg/mL. Both HHT888-4 and HHT888-5 were cytotoxic (<50% of control) at 25 mg/mL level.

Table 3 summarizes the cytotoxicity and the HIV suppression test results of HHT888-4 and HHT888-5, as well as the AZT controls. Both herb mixtures were active in suppressing HIV proliferation in infected human lymphocytes at 2.5–5.0 mg/mL, but not at 50 µg/mL (50–100 times diluted). The AZT controls from all sets of anti-HIV assays herein and thereinafter exhibited the expected activities and thus assured the validity of the tests.

At 2.5–5.0 mg/mL of HHT888-4 and HHT888-5, HIV proliferation in infected human lymphocytes were essentially completely suppressed: 97–100% suppression based was transferred into a clean preweighed 50-mL centrifuge tube, freeze dried, weighed, and tested for anti-HIV activity.

The percent weight of material extracted was 17.3% for the first 25 mL extract and 10.8% for the second 25 mL extract of HHT888-4 (Lot 2). That was 14.2% for the first 25 mL extract and 4.6% for the second 25 mL extract of HHT888-5 (Lot 2). The first (E1), the second (E2) and the combined (E) extracts of HHT888-4 (Lot 2) were tested for anti-HIV activity. All the other extracts were tested with the first and the second extracts combined. The results are summarized also in Table 4.

TABLE 4

Anti-HIV Activities of HHT888-4 and HHT888-5 and their Water Extracts

| Sample | Lot | % Weight | Test Concentration | Cytotoxicity* | HIV Suppression** Day 3 | Day 4 |
|---|---|---|---|---|---|---|
| HHT888-4 | 1 | 100% | 2.5 mg/mL | >46% | 100% | 100% |
|  |  |  | 2.5 mg/mL | 98% | 100% | 100% |
|  |  |  | 0.05 mg/mL | 85% | 1% | 6% |
|  | 2 | 100% | 2.5 mg/mL | 100% | 100% | 100% |
|  | 3*** | 100% | 2.5 mg/mL | 71–79% | 100% | 100% |
| HHT888-4-E1 | 2 | 17% | 1.0 mg/mL | 98% | 100% | 96% |
| E2 | 2 | 11% | 1.0 mg/mL | 96% | 100% | 87% |
| E | 2 | 28% | 1.0 mg/mL | 47% | 100% | 100% |
|  |  |  | 0.5 mg/mL | 78% | 100% | 100% |
|  | 4 | 27 ± 1% (2) | 1.0 mg/mL | 72% | 100% | 100% |
|  |  |  | 1.0 mg/mL | 100% | 100% | 93% |
|  |  |  | 0.1 mg/mL | 97% | 34% | 12% |
|  |  |  | 0.02 mg/mL | 82% | 23% | 2% |
| HHT888-5 | 1 | 100% | 5.0 mg/mL | 75% | 100% | 97% |
|  |  |  | 2.5 mg/mL | 89% | 93% | 91% |
|  |  |  | 0.05 mg/mL | 86% | 0% | 12% |
|  | 2 | 100% | 2.5 mg/mL | 91% | 94% | 89% |
|  | 3** | 100% | 2.5 mg/mL | 44–85% | 98% | 99% |
|  |  |  | 0.5 mg/mL | 52–100% | 0% | 0% |
| HHT888-5-E | 2 | 19% | 1.0 mg/mL | 91% | 71% | 26% |

*Toxicity in percent of control proliferation.
**HIV suppression based on viral protein p24 levels.
***Composite of respective single herb components at equal proportions. No. 5(10) and No. 5(11) were not included in Lot 3 of HHT888-5.

All three Lots of each of the herb mixtures were very active, 100% suppression at 2.5 mg/mL for HHT888-4 and 89–100% suppression at 2.5–5.0 mg/mL for HHT888-5. The $IC_{50}$ was between 0.05–2.5 mg/mL for HHT888-4 and between 0.5-2.5 mg/mL for HHT888-5. $IC_{50}$ is the concentration of the test substance at which would cause 50% suppression of the viral proliferation.

The water extract of HHT888-4 showed very good activity: 93–100% suppression at 0.5–1.0 mg/mL. The first (E1) and the second water extract (E2) of Lot 2 exhibited comparable activities: 100% suppression on day 3 and 87–96% suppression on day 4 at 1.0 mg/mL. The $IC_{50}$ of the water extract of HHT888-4 was between 0.1–0.5 mg/mL.

The water extract of HHT888-5 (lot 2) exhibited a substantially lower activity: 71% suppression on day 3 which dropped to 26% suppression on day 4 at 1.0 mg/mL. The main active component apparently stayed behind in the insoluble fraction and was not as easily extracted by water as that of HHT888-4 under the aforementioned conditions. It is noted that the water extract of HHT888-5 (Lot 2) constituted 19% by weight of the herb mixture. The test concentration of the water extract of HHT888-5 (or HHT888-5-E) at 1.0 mg/mL is equivalent to 5.3 mg/mL of HHT888-5 itself. HHT888-5 was tested very active at both 2.5 mg/mL (93–98% suppression on day 3 and 89–99% on day 4) and 5.0 mg/mL (100% suppression on day 3 and 97% on day 4).

The above results clearly demonstrated that both HHT888-4 and HHT888-5 and their water extracts have in vitro antiretroviral activities, more specifically anti-EMuLV and anti-HIV activities. HHT888-5 has also been shown to be efficacious in treating hepatitis B virus carriers, while HHT888-4 has not been tested in vivo.

EXAMPLE 5

Antiretroviral Testing of Individual Single-herb Herbal Medicines

The individual single-herb components of HHT888-4 and HHT888-5 were tested for anti-HIV activity. Table 5 shows the test results.

TABLE 5

Anti-HIV Activities of Single-herb Components of HHT888-4 and HHT888-5

| Sample | Lot | Test Concentration | Cytotoxicity* | HIV Suppression** Day 3 | Day 4 |
|---|---|---|---|---|---|
| No. 4(1)** | 1 | 2.5 mg/mL | 98% | 73% | 50% |
| No. 4(2) | 1 | 2.5 mg/mL | 74–84% | 92% | 94% |
| No. 4(3) | 1 | 2.5 mg/mL | 75–78% | 100% | 100% |
| No. 4(4) | 1 | 2.5 mg/mL | 74–100% | 100% | 100% |
| No. 4(5) | 1 | 2.5 mg/mL | 41–79% | 98% | 92% |
|  |  | 0.5 mg/mL | 47–100% | 0% | 0% |
| No. 5(1)*** | 1 | 2.5 mg/mL | 98% | 73% | 50% |
| No. 5(20) | 1 | 2.5 mg/mL | 73–87% | 18% | 29% |
| No. 5(3) | 1 | 2.5 mg/mL | 89–100% | 0% | 0% |
| No. 5(4) | 1 | 2.5 mg/mL | 64% | 100% | 100% |
|  |  | 1.0 mg/mL | 69–91% | 0% | 0% |
| No. 5(5) | 1 | 2.5 mg/mL | 80–84% | 93% | 93% |
| No. 5(6) | 1 | 2.5 mg/mL | 94–100% | 0% | 0% |
| No. 5(7) | 1 | 2.5 mg/mL | 90–100% | 50% | 38% |
| No. 5(8) | 1 | 2.5 mg/mL | 32–59% | 100% | 100% |
|  |  | 0.5 mg/mL | 65–100% | 0% | 0% |
| No. 5(9) | 1 | 0.5 mg/mL | 24–78% | 0% | 0% |
| No. 5(10) | 1 | 2.5 mg/mL | 100% | 65% | 0% |
| No. 5(11) | 1 | 2.5 mg/mL | 100% | 92% | 74% |

*Toxicity in percent of control proliferation.
**HIV suppression based on viral protein p24 levels.
No. 4(1) = No. 5(1)

All five (5) single-herb components of HHT888-4 exhibited anti-HIV activities with various degrees: 73–100% suppression on day 3 and 50–100% suppression on day 4 at 2.5 mg/mL. No. 4(3) and No. 4(4) exhibited the best activity: 100% suppression at 2.5 mg/mL on both day 3 and day 4. No. 4(2) and No. 4(5) were the next: 92–98% suppression on day 3 and 92–94% suppression on day 4 at 2.5 mg/mL. No.4(1) exhibited a moderate activity: 73% suppression on day 3 and 50% suppression on day 4 at 2.5 mg/mL. No.4(5) exhibited a slight cytotoxicity (41–79% of control proliferation) which was likely to contribute to the observed activity with an $ID_{50}$ between 0.5 and 2.5 mg/mL.

Three (3) of the eleven (11) single-herb components of HHT888-5: No.5(4), No.5(5), and No.5(8) exhibited very good activities, 93–100% suppression of HIV proliferation on both day 3 and day 4 at 2.5 mg/mL. No.5(11) was the next: 92% suppression on day 3 and 74% suppression on day 4 at 2.5 mg/mL. Again, No.5(1), which was the same as No.4(1), had a moderate activity: 73% suppression on day 3 and 50% suppression on day 4 at 2.5 mg/mL. No.5(2) and No.5(7) exhibited only marginal activities: 18–50% suppression on day 3 and 29–38% suppression on day 4 at 2.5 mg/mL. No.5(10) exhibited a very slight activity: 65% suppression on day 3 which dropped to 0% on day 4 at 2.5 mg/mL. The remaining three (3) single-herb components, No.5(3), No.5(6), and No.5(9) exhibited no activity at 0.5–2.5 mg/mL. No.5(9) was not tested at 2.5 mg/mL level because of its cytotoxicity: already 24–78% of control proliferation at 0.5 mg/mL.

Although No.5(4) and No.5(8) appeared to be slightly more active than No.5(5) (100% vs. 93% suppression at 2.5 mg/mL), their activities might be partially due to cytotoxicity (32–64% of control proliferation at 2.5 mg/mL). This was supported by the loss of activity (0% suppression) when tested at lower levels, 0.5–1.0 mg/mL, where the cytotoxicity was lower and more acceptable to the assay.

EXAMPLE 6

Anti-HIV Testing of Medicinal Plant

The source plant of the single-herb herbal medicine No.5(5), *Aeginetia indica*, was obtained from a local herbal store in Taiwan and tested for its anti-HIV activity. This was to see whether the activity can be reproduced in the herbal medicine prepared directly from its source plant, instead of being obtained from the commercial source.

The whole plant was washed with cold water, dried, comminuted, and extracted with boiling water as described above in Example 2. The aqueous solution was separated from the plant material by filtration. The aqueous solution was then reduced in volume by heating. The concentrate was spray dried and absorbed onto powdered material of the same plant material and thus was prepared the herbal medicine in powder form, designated hereinafter as raw No.5(5).

The powdered herbal medicine prepared from *Aeginetia indica*, or raw No.5(5), was extracted with water at ambient temperature. Two (2) 5.00 g samples were each extracted twice with about 40 mL of water each time in a separate 50-mL plastic centrifuge tube by vortexing for one (1) minute, standing for ten (10) minutes, and vortexing again for one (1) minute. The tubes were centrifuged at 1500 rpm for twenty (20) minutes to separate the extracts from the insoluble residues. The extracts were filtered through a Whatman No.4 filter paper, freeze dried or nitrogen dried, and weighed.

The above extraction of the raw No.5(5) with water (pH~5.1) was repeated and the pH of the first extract was measured to be 5.7. The first and the second extracts were respectively separated from the residue, air dried, and weighed. The percent weight of the extractable was determined to be 18.7±2.8% (n=2).

The first water extract of the raw No.5(5) was tested for anti-HIV activity and found to be as active, 91% suppression on day 3 and 97% suppression on day 4 at 1.0 mg/mL. Cytotoxicity test showed that the extract was not cytotoxic at this level, 99% of control proliferation.

The above examples clearly demonstrate that both the herb mixtures HHT888-4 and HHT888-5 are very active against HIV proliferation. Complete (100%) or nearly complete (89–99%) suppressions of HIV proliferation were achieved at 2.5 mg/mL. The water extract of HHT888-4 is also very active. Complete (100%) suppression of HIV proliferation was achieved at 0.5 mg/mL. The water extract of HHT888-5 is not as active as its original mixture. It only suppressed 26–71% of HIV proliferation at 1.0 mg/mL. Both HHT888-4 and HHT888-5 are not cytotoxic at 2.5 mg/mL. The water extracts of both HHT888-4 and HHT888-5 are also not cytotoxic at 1.0 mg/mL.

HHT888-5 has been demonstrated to be effective and safe in treating HBV infections in humans. That means, the active principle or principles of HHT888-5 must be bioavailable in humans through oral administration to cause the decrease of hepatitis B virus in those patients treated, as indicated by the decrease of their hepatitis B virus surface antigen (HBsAg) exhibited in Example 3. In addition, Hozumi et al. provide examples in U.S. Pat. No. 5,411,733 to support the belief that substances exhibiting antiviral activity in vitro also possess antiviral activity in vivo as described in the Prior Art section. It is therefore logical to believe that HHT888-4 or HHT888-5 and their water extracts or active principles should also be effective for treating HIV infections in humans.

To test the belief, six (6) of the most anti-HIV active single-herb components of HHT888-4 and HHT888-5 were selected to treat hepatitis C patients caused by hepatitis C virus infections. The logic is that both HCV and HIV are retroviruses. Viral hepatitis C tends to become a chronic disease and is therefore more suitable for the test of the treatment. If the treatment works for patients infected with HCV, it will also work for patients infected with HIV. Example 7 clearly demonstrates the validity of this belief.

EXAMPLE 7

Treatment of Hepatitis C Patients

Six (6) of the most anti-HIV active single-herb components of HHT888-4 and HHT888-5 were selected and mixed to treat hepatitis C patients caused by hepatitis C virus infections. The six (6) single-herb herbal medicines selected were No.4(2), No.4(3), No.4(4), No.5(4), No.5(5), and No.5(8). No.4(5) was not included although it exhibited a very good activity because it was learned that the herb might have a certain unconfirmed toxicity.

The six (6) single-herb herbal medicines were obtained from a commercial source and were manufactured following good manufacture practice (GMP) guidelines. They were mixed according to the desired ratio in various combinations and thus the herb mixture HHT888-45 was prepared as further described in Example 1. Patients' consents were obtained before the initiation of treatment.

Patients were instructed to take the herb mixture three (3) times a day, 2.7–5.7 g each time. Unit dosages of the herb mixture HHT888-45 were prepared in individual packets. Each unit dose packet (2.7–5.7 g) of the herb mixture was mixed with warm water and taken orally. All patients were treated with HHT888-45 containing No.4(3), No.4(4), No.5(4), and No.5(5). No.5(8) or No.4(2) or both were added in HHT888-45 for the treatment of some patients at the very beginning or during the course of the treatment to enhance the effectiveness of the treatment. During the course of the treatment, the daily dose of No.4(3), No.4(4), No.5(4), and No.5(5) varied from two (2) to three (3) g each. The daily dose of No.5(8) also varied from two (2) to three (3) g when used. The daily dose of No.4(2) varied from 1.5 to two g when used. The dose was varied according to the progress of the disease.

Seven (7) viral hepatitis C patients were treated. Their serum liver enzymes, SGOT and SGPT, were determined from time to time by a local clinical laboratory during the course of the treatment to monitor the progress of the disease. The SGOT and SGPT were determined using an enzyme assay. See (1) Instruction of Kyokuto TA-E Transaminase Assay Reagents, Permit No. (62AM)0885, Kyokuto Pharmaceutical Industry Co., Ltd., Tokyo, Japan, 1994; (2) Instruction of Yatrozyme TA-Lq Transaminase-assay Reagent Solution (Enzyme Assay), Commodity No. 817245 (RM163-K), Yatron Co., Ltd., Diayatron Co., Ltd., Tokyo, Japan; and (3) U. Lippi & G Guidi, Clin. Chim. Acta., 28, 431–437 (1970).

The levels of serum GOT and GPT closely correlate with the degree of cellular injury in the liver. These tests are widely used in the diagnosis of liver diseases and as an indicator of the liver function. The normal range for SGOT is 8–40 units/mL and that for SGPT is 5–35 units/mL. Elevated SGOT and SGPT levels usually indicate compromised liver functions.

The results of HHT888-45 treatment are shown in Table 6. All seven (7) patients treated had their serum liver enzymes returned from elevated levels (SGOT from 48 to 166 unit/mL and SGPT from 41 to 291 unit/mL) to essentially normal range (SGOT from 8 to 40 unit/mL and SGPT from 5 to 35 unit/mL) after 17 to 178 days of treatment. Thus, the liver functions of the patients were returned to normal after consumption of the invention composition.

The results clearly demonstrate that the herb mixture HHT888-45 is effective in treating hepatitis C patients. To accomplish that, the causative hepatitis C virus needs to be eradicated or reduced to a tolerable level. Since HHT888-45 components have demonstrated very strong anti-HIV in vitro activity and several of the components have demonstrated efficacy in reducing HBV in carriers, the herb mixture will therefore be effective in treating patients infected with HIV and HBV.

It is therefore an aspect of this invention that the antiviral herbal medicines including the herb mixtures according to this invention and their single-herb components at various proportions and effective doses are effective in treating hepatitis C, hepatitis B, and other retroviral diseases, such as AIDS.

TABLE 6

Clinical Effect Of HHT888-45* On Type C Hepatitis Patients

| Patient | SGOT**, unit/mL | | SGPT**, unit/mL | | Duration |
|---|---|---|---|---|---|
| | Before | After | Before | After | (days) |
| 1 | 112 | 53 | 238 | 146 | 3 |
| | | 30 | | 35 | 64 |
| | | 16 | | 18 | 77 |
| 2 | 81 | 35 | 103 | 62 | 9 |
| | | 41 | | 61 | 20 |
| | | 46 | | 67 | 29 |
| | | 32 | | 56 | 37 |
| | | 21 | | 43 | 53 |
| | | 24 | | 50 | 70 |
| | | 23 | | 43 | 85 |
| | | 28 | | 55 | 102 |
| | | 23 | | 44 | 117 |
| | | 23 | | 29 | 178 |
| 3 | 117 | 96 | 179 | 123 | 8 |
| | | 75 | | 74 | 19 |
| | | 66 | | 69 | 26 |
| | | 47 | | 51 | 34 |
| | | 55 | | 48 | 42 |
| | | 42 | | 45 | 50 |
| | | 48 | | 40 | 70 |
| | | 38 | | 32 | 79 |

TABLE 6-continued

Clinical Effect Of HHT888-45* On Type C Hepatitis Patients

| Patient | SGOT**, unit/mL | | SGPT**, unit/mL | | Duration |
|---|---|---|---|---|---|
| | Before | After | Before | After | (days) |
| | | 30 | | 26 | 88 |
| 4 | 48 | 32 | 71 | 65 | 56 |
| | | 30 | | 55 | 70 |
| | | 21 | | 37 | 87 |
| 5 | 83 | 64 | 67 | 54 | 8 |
| | | 58 | | 46 | 14 |
| | | 56 | | 40 | 22 |
| | | 42 | | 34 | 29 |
| | | 38 | | 28 | 36 |
| 6 | 166 | 106 | 291 | 206 | 2 |
| | | 71 | | 121 | 16 |
| | | 51 | | 81 | 22 |
| | | 57 | | 89 | 29 |
| | | 36 | | 45 | 45 |
| | | 31 | | 36 | 50 |
| | | 28 | | 37 | 58 |
| | | 22 | | 29 | 64 |
| | | 28 | | 32 | 71 |
| | | 25 | | 27 | 85 |
| | | 36 | | 28 | 103 |
| | | 23 | | 27 | 113 |
| | | 23 | | 22 | 163 |
| 7 | 30 | 28 | 41 | 42 | 9 |
| | | 29 | | 32 | 17 |

*Comprising mainly Nos. 4(3), 4(4), 5(4) and 5(5), and occasionally 4(2) and 5(8).
**SGOT = serum glutamine oxalacetate transferase; normal range = 8–40 unit/mL.
SGPT = serum glutamine pyruvate transferase; normal range = 5–35 unit/mL.

Since the precise chemical composition and pharmacological mechanism of the compositions of this invention have not yet been eludicated, it is possible that the antiviral activity may be due to a single herbal component, a combination of components or the biological metabolite or derivative thereof.

Industrial Applicability

The instant invention is directed in part, to the discovery that specific medicinal plants or herbal medicines or their mixtures possess surprising antiviral activities without causing damage to the host cells. Further, the invention is directed to methods of treating humans and mammals infected with viruses such as HBV, HCV, or HIV. The data presented in this application clearly demonstrate that the identified compositions possess antiviral activity without toxicity to the host cells.

It can be concluded from the foregoing experiments that the herb mixture designated HHT888-4 is effective in treating HBV carriers and thus can be used to treat humans infected with HBV. The reduction of viral load in HBV patients will thus result in the prevention of HBV disease in the human and will also be effective in the treatment of humans exhibiting HBV disease. The clinical experiments have also shown that the herb mixture HHT888-45 is effective in treating hepatitis C patients, and thus is expected to be effective in treating hepatitis B patients when administered alone or in combination with HHT888-5 or its antiviral single-herb components.

In addition, HHT888-5, HHT888-45, HHT888-54 and the individual anti-HIV active single-herb components have demonstrated efficacy in suppressing HIV proliferation in human cells. Furthermore, HHT888-5, HHT888-45 and HHT888-54 have shown efficacy in treating patients infected with HBV and HCV. HHT888-5, HHT888-45, HHT888-4 and HHT888-54 are also effective in treating humans infected with HIV, including HIV carriers and AIDS patients.

The therapeutic effects described herein may be accomplished through the administration of the herbal medicines "as is", or as teas, decoctions, beverages, candies or other confections, enteral liquid nutritional products such as infant formula and adult nutritional products, medical foods, nutritional supplements or neutraceuticals containing one or more of the herbal medicines or their extracts or active principles. For pharmaceutical preparations, one or more of the antiviral herbal medicines or their extracts or active principles described above may be administered in unit dosage forms such as capsules, packets or tablets, with or without controlled-release coating(s).

The medical community is constantly in search of methods and products that will effectively treat viral infections, especially methods and products for treating humans infected with HBV, HCV, and HIV. The herb mixtures HHT888-4, HHT888-5, HHT888-45, HHT888-54, the single-herb components, their extracts, active principles, and products containing these herbal compositions will be readily accepted by the medical community as an additional tool in the prevention and treatment of these devastating illnesses.

While certain representative embodiments have been described herein, it will be apparent to those skilled in the art that various changes and modifications may be made therein without departing from the spirit or scope of this invention.

We claim:

1. A method for treating a subject having a viral infection selected from the group consisting of hepatitis B virus (HBV), hepatitis C virus (HCV), leukemia virus (LV) and human immunodeficiency virus (HIV), said method comprising administering to said subject in need thereof, a therapeutically effective amount of a composition which comprises at least one herbal medicine selected from the group consisting of:
   a) SOLANI HERBA, prepared from the whole plant of *Solanum nigrum;*
   b) LESPEDEZAE HERBA, prepared from the whole plant of *Lespedeza cuneata;*
   c) SENECINIS HERBA, prepared from the whole plant of *Senecio scandens;* and
   d) LIGUSTRI FRUCTUS, prepared from the mature fruit of at least one plant selected from the group consisting of *Ligustrum lucidum* and *Ligustrum japonicum.*

2. The method of claim 1 wherein said composition additionally comprises at least one herbal medicine selected from the group consisting of:
   a) HEDYOTIS, prepared from the whole plant of *Hedyotis diffusa;*
   b) SCUTELLARIAE BARBATAE HERBA, prepared from the whole plant of at least one selected from the group consisting of *Scutellaria barbata, Scutellaria rivularis* and *Scutellaria dependens;*
   c) LONICERAE FLOS, prepared from the flower bud of at least one plant selected from the group consisting of *Lonicera japonica* and *Lonicera confusa;*
   d) PRUNELLAE SPICA, prepared from the spica or whole plant of at least one plant selected from the group consisting of *Prunella vulgaris* and *Prunella vulgaris* subsp. *asiatica;*
   e) BLECHNI RHIZOMA, prepared from at least one plant selected from the group consisting of *Blechnum orientate, Osmunda japonica, Woodwardia orientalis, Woodwardia unigemmata, Athyrium acrostichoides, Sphaeropteris lepifera, Cyrtomium falcatum* and *Cyrtomium fortunei;*
   f) DRYOPTERIS CRASSIRHIZOMAE RHIZOMA, prepared from at least one plant selected from the group consisting of *Dryopteris crassirhizoma, Osmunda japonica, Woodwardia orientalis, Woodwardia unigemmata, Athyrium acrostichoides, Sphaeropteris lepifera, Cyrtomium falcatum* and *Cyrtomium fortunei:*
   g) CIRSII RHIZOMA ET RADIX, prepared from the rhizome, root or whole plant of at least one plant selected from the group consisting of *Cirsium japonicum, Cirsium albescens* and *Cirsium japonicum* vat. *australe;*
   h) BREEAE RADIX, prepared from the root of at least one plant selected from the group consisting of *Breea segetum* and *Breea setosum;*
   i) AEGINETIAE HERBA, prepared from the whole plant of at least one plant selected from the group consisting of *Aeginetia indica, Dichondra micrantha, Striga lutea* and *Dichondra repens;*
   j) BAPHICACANTHIS RHIZOMA ET RADIX, prepared from the rhizome or root of at least one plant selected from the group consisting of *Baphicacanthes cusia, Strobilanthes cusia, Isatis tinctoria, Isatis indigotica* and *Polygonum tinctorium;*
   k) POLYGONI CUSPIDATI RHIZOMA, prepared from the rhizome of at least one plant selected from the group consisting of *Polygonum cuspidatum, Polygonum runcinatum* and *Polygonum reynoutria;*
   l) FORSYTHIAE FRUCTUS, prepared from the mature fruit of at least one plant selected from the group consisting of *Forsythia suspensa, Forsythia viridissima* and *Forsythia koreana;*
   m) PHELLODENDRI CORTEX, prepared from the cortex of at least one plant selected from the group consisting of Phellodendron amurense, Phellodendron chinense, Phellodendron amurensevar. *sachalinense* and *Phellodendron wilsonii;* and
   n) BLETILLAE TUBER, prepared from the tuber of *Bletilla striata.*

3. The method according to claim 2 wherein said composition comprises:
   a) HEDYOTIS;
   b) SCUTELLARIAE BARBATAE HERBA;
   c) LONICERAE FLOS;
   d) PRUNELLAE SPICA; and
   e) SOLANI HERBA.

4. The method according to claim 3 wherein the weight ratio of a:b:c:d:e is about 3:3:3:3:4.

5. The method according to claim 2 wherein said comtposition comprises:
   a) HEDYOTIS;
   b) AEGINETIAE HERBA;
   c) BAPHICACANTHIS RHIZOMA ET RADIX;
   d) POLYGONI CUSPIDATI RHIZOMA;
   e) FORSYTHIAE FRUCTUS;
   f) PHELLODENDRI CORTEX
   g) BLETILLAE TUBER; and
   h) LIGUSTRI FRUCTUS.

6. The method of claim 2 wherein said composition comprises:
   a) LONICERAE FLOS;
   b) PRUNELLAE SPICA;
   c) AEGINETIAE HERBA; and
   d) at least one herbal medicine selected from the group consisting of LESPEDEZAE HERBA and SENECINIS HERBA.

7. The method of 2, 3, 5 or 6 wherein said therapeutically effective amount is 0.4 to 120 grams per day.

8. The method of claims 2, 3, 5 or 6 wherein said composition is administered as a beverage, capsule, tablet, powder, candy, gel, nutritional product or pharmaceutical product.

9. A method for treating a subject having a viral infection selected from the group consisting of HIV, LV, and HCV, said method comprising administering to said subject in need thereof, a therapeutically effective amount of a composition comprising at least one herbal medicine selected from the group consisting of:

a) HEDYOTIS, prepared from the whole plant of *Hedyotis diffusa;* b) AEGINETIAE HERBA, prepared from the whole plant of at least one plant selected from the group consisting of *Aeginetia indica, Dichondra micrantha, Striga lutea* and *Dichondra repens;* c) SCUTELLARIAE BARBATAE HERBA, prepared from the whole plant of at least one plant selected from the group consisting of *Scutellaria barbata, Scutellaria rivularis* and *Scutellaria dependens;* and d) FORSYTHIAE FRUCTUS, prepared from the mature fruit of at least one plant selected from the group consisting of *Forsythia suspensa, Forsythia viridissima* and *Forsythia koreana.*

10. The method of claim 9 wherein said composition comprises:

a) AEGINETIAE HERBA; and b) at least one herbal medicine selected from the group consisting of:

(i) SCUTELLARIAE BARBATAE HERBA;

(ii) HEDYOTIS;

(iii) FORSYTHIAE FRUCTUS;

(iv) LONICERAE FLOS, prepared from the flower bud of at least one plant selected from the group consisting of *Lonicera japonica* and *Lonicera confusa;*

(v) PRUNELLAE SPICA, prepared from the spica or whole plant of at least one plant selected from the group consisting of *Prunella vulgaris* and *Prunella vulgaris* subsp. *asiatica;*

(vi) POLYGONI CUSPIDATI RHIZOMA, prepared from the rhizome of at least one plant selected from the group consisting of *Polygonum cuspidatum, Polygonum runcinatum* and *Polygonum reynoutria;*

(vii) BLECHNI RHIZOMA, prepared from at least one plant selected from the group consisting of *Blechnum orientale, Osmunda japonica, Woodwardia orientalis, Woodwardia unigemmata, Athyrium acrostichoides, Sphaeropteris lepifera, Cyrtomium falcatum* and *Cyrtomium fortunei;* and (viii) DRYOPTERIS CRASSIRHIZOMAE RHIZOMA, prepared from the plant Dryopteris crassirhizoma.

11. The method of claim 10 wherein said therapeutically effective amount is 0.4 to 120 grams per day.

12. The method of claim 10 wherein the weight ratio of a) to b) is from 1:10 to 10:1.

13. The method of claim 10 wherein said composition is administered as a beverage, capsule, tablet, powder, candy, gel, nutritional product or pharmaceutical product.

* * * * *